United States Patent
Vasu et al.

(10) Patent No.: US 10,066,000 B2
(45) Date of Patent: Sep. 4, 2018

(54) HIGH YIELD TRANSIENT EXPRESSION IN MAMMALIAN CELLS USING UNIQUE PAIRING OF HIGH DENSITY GROWTH AND TRANSFECTION MEDIUM AND EXPRESSION ENHANCERS

(71) Applicant: LIFE TECHNOLOGIES CORPORATION, Carlsbad, CA (US)

(72) Inventors: Sanjay Vasu, Carlsbad, CA (US); Henry Chiou, Encinitas, CA (US); Jeffrey Rogers, Escondido, CA (US); Maria Isabel Cisneros, San Marcos, CA (US); Jingqiu Li, San Diego, CA (US); Chao Yan Liu, Clarence Center, NY (US); Meredith Jones, Chapel Hill, NC (US)

(73) Assignee: Life Technologies Corporation, Carlsbad, CA (US)

( * ) Notice: Subject to any disclaimer, the term of this patent is extended or adjusted under 35 U.S.C. 154(b) by 970 days.

(21) Appl. No.: 13/886,226

(22) Filed: May 2, 2013

(65) Prior Publication Data

US 2013/0316400 A1  Nov. 28, 2013

Related U.S. Application Data

(60) Provisional application No. 61/641,864, filed on May 2, 2012.

(51) Int. Cl.

| | |
|---|---|
| *C12P 21/02* | (2006.01) |
| *C12N 5/02* | (2006.01) |
| *C07K 14/505* | (2006.01) |
| *C12N 5/00* | (2006.01) |
| *C12N 5/07* | (2010.01) |
| *C12N 5/073* | (2010.01) |
| *C12N 5/10* | (2006.01) |
| *C12N 5/16* | (2006.01) |
| *C12N 5/22* | (2006.01) |

(52) U.S. Cl.
CPC ............ *C07K 14/505* (2013.01); *C12N 5/005* (2013.01); *C12N 2500/30* (2013.01); *C12N 2501/065* (2013.01); *C12N 2501/999* (2013.01); *C12N 2510/02* (2013.01); *C12N 2511/00* (2013.01)

(58) Field of Classification Search
None
See application file for complete search history.

(56) References Cited

U.S. PATENT DOCUMENTS

| | | | |
|---|---|---|---|
| 5,378,612 A | * | 1/1995 | Nakashima .......... C07K 14/755 435/404 |
| 8,871,439 B2 | | 10/2014 | Schroeder et al. |
| 2003/0096414 A1 | | 5/2003 | Ciccarone et al. |
| 2007/0254358 A1 | | 11/2007 | Ciccarone et al. |
| 2008/0145893 A1 | | 6/2008 | Hildinger et al. |
| 2009/0023186 A1 | | 1/2009 | Hildinger et al. |
| 2013/0316400 A1 † | | 11/2013 | Vasu |
| 2014/0057335 A1 | | 2/2014 | Ciccarone et al. |

OTHER PUBLICATIONS

Liu et al., "Transient Transfection Factors for High-Level Recombinant Protein Production in Suspension Cultured Mammalian Cells" 39 Molecular Biotechnology 141-153 (2008).*

Zufferey et al., "Woodchuck Hepatitis Virus Posttranscriptional Regulatory Element Enhances Expression of Transgenes Delivered by Retroviral Vectors" 73(4) Journal of Virology 2886-2892 (1999).*

Chun et al., "Enhanced production of recombinant B-domain deleted factor VIII from Chinese hamster ovary cells by propionic and butyric acids" 25 Biotechnology Letters 315-319 (2003).*

Backliwal, G. et al., "Coexpression of acidic fibroblast growth factor enhances specific productivity and antibody titers in transiently transfected HEK293 cells", *New Biotechnology*, vol. 25(2/3), 2008, pp. 162-166.

Backliwal, G. et al., "High-Density Transfection With HEK-293 Cells Allows Doubling of Transient Titers and Removes Need for a Priori DNA Complex Formation With PEI", *Biotechnology and Bioengineering*, vol. 99(3), Feb. 15, 2008, pp. 721-727.

Backliwal, G. et al., "Rational vector design and multi-pathway modulation of HEK 293E cells yield recombinant antibody titers exceeding 1 g/l by transient transfection under serum-free conditions", *Nucleic Acids Research*, vol. 36(15), Jul. 24, 2008, pp. 1-7.

Backliwal, G. et al., "Valproic Acid: A Viable Alternative to Sodium Butyrate for Enhancing Protein Expression in Mammalian Cell Cultures", *Biotechnology and Bioengineering*, vol. 101(1), Sep. 1, 2008, pp. 182-189.

Baldi, L. et al., "Large-scale transfection of mammalian cells", *Methods in Molecular Biology*, vol. 801, Chapter 12, Jan. 1, 2012, 13-26.

Baldi, L. et al., "Recombinant protein production by large-scale transient gene expression in mammalian cells: state of the art and future perspectives", *Biotechnology Letters*, vol. 29(5), Jan. 19, 2007, 677-684.

(Continued)

*Primary Examiner* — Nancy J Leith

(57) ABSTRACT

High-Yield mammalian transient expression systems can include a cell culture media (particularly serum free, non animal derived, and/or chemically defined media) for introducing macromolecules and compounds (e.g., nucleic acid molecules) into cells (e.g., eukaryotic cells). Cells containing such introduced materials can then be cultured in the cell culture media. In particular, the invention allows introduction of nucleic acid molecules (e.g., vectors) into cells (particularly mammalian cells) and expression of proteins encoded by the nucleic acid molecules in the cells. The invention obviates the need to change the cell culture medium each time a different procedure is performed with the cells (e.g., culturing cells vs. transfecting cells). The invention also relates to compositions and kits useful for culturing and transforming/transfecting cells.

30 Claims, 4 Drawing Sheets

(56) References Cited

OTHER PUBLICATIONS

Invitrogen Corporation, , "Free-Style MAX 293 Expression System; For large-scale transfection of suspension 293 cells in a defined, serum-free medium", *Catalog No. K9000-10*, Version C, Oct. 28, 2010, pp. i-20.
PCT/US2013/039351 Partial International Search Report dated Jul. 5, 2013.
Phuong, L. et al., "Transfection of Mammalian Cells for the Fast Production of Recombinant Protein", *Molecular Biotechnology*, vol. 34(2), Oct. 1, 2006, 225-238.
Sun, X. et al., "High-density transient gene expression in suspension-adapted 293 EBNA1 cells", *Biotechnology and Bioengineering*, vol. 99(1), Jul. 13, 2007, 108-116.
Wulhfard, S. et al., "Valproic acid enhances recombinant mRNA and protein level in transiently transfected Chines hamster ovary cells", *J. Biotechnology*, vol. 148 (2-3), Jul. 20, 2010, 128-132.
PCT/US2013/039351 Notification of Transmittal of the International Search Report and the Written Opinion of the International Searching Authority dated Sep. 30, 2013, pp. 1-26.
EP2844737, "Third Party Observation for application No. EP20130722946 filed", 4 Pages, Aug. 23, 2017.
Ido, Hiroyuki et al., "Molecular Dissection of the alpha-Dystroglycan- and Integrin-binding Sites within the Globular Domain of Human Laminin-10", *The Journal of Biological Chemistry*, vol. 279, No. 12, Mar. 19, 2004, 10946-10954.

\* cited by examiner
† cited by third party

HIGH YIELD TRANSIENT EXPRESSION IN MAMMALIAN CELLS USING UNIQUE PAIRING OF HIGH DENSITY GROWTH AND TRANSFECTION MEDIUM AND EXPRESSION ENHANCERS

CROSS-REFERENCE TO RELATED APPLICATIONS

This application claims the right of priority under 35 U.S.C. § 119(e) to U.S. Provisional Application Ser. No. 61/641,864, filed May 2, 2012, which is commonly owned with the present application and which the entire contents thereof are hereby expressly incorporated by reference as though fully set forth herein.

FIELD OF THE INVENTION

The present invention generally relates to the fields of transfection and cell culture. In particular, the present invention provides a transfection system suitable for yield expression of recombinant proteins in cultured mammalian cells. The invention further related to systems and methods for high yield expression of recombinant proteins in mammalian cells.

BACKGROUND

Cell culture media provide the nutrients necessary to maintain and grow cells in a controlled, artificial and in vitro environment. Characteristics and formulations of cell culture media vary depending upon the particular cellular requirements. Important parameters include osmolarity, pH, and nutrient compositions.

Cell culture medium formulations have been well documented in the literature and a large number of media are commercially available. In early cell culture work, medium formulations were based upon the chemical composition and physicochemical properties (e.g., osmolality, pH, etc.) of blood and were referred to as "physiological solutions" (Ringer, S., J. Physiol. 3:380-393 (1880); Waymouth, C., In: Cells and Tissues in Culture, Vol. 1, Academic Press, London, pp. 99-142 (1965); Waymouth, C., In Vitro 6:109-127 (1970)). However, cells in different tissues of a mammalian body are exposed to different microenvironments with respect to oxygen/carbon dioxide partial pressure and concentrations of nutrients, vitamins, and trace elements; accordingly, successful in vitro culture of different cell types may require the use of different medium formulations. Typical components of cell culture media include amino acids, organic and inorganic salts, vitamins, trace metals, sugars, lipids and nucleic acids, the types and amounts of which may vary depending upon the particular requirements of a given cell or tissue type.

Medium formulations have been used to cultivate a number of cell types including animal, plant and bacterial cells. Cultivated cells have many uses including the study of physiological processes and the production of useful biological substances. Examples of such useful products include monoclonal antibodies, hormones, growth factors, enzymes and the like. Such products have many commercial and therapeutic applications and, with the advent of recombinant DNA technology, cells can be engineered to produce large quantities of these products. Cultured cells are also routinely used for the isolation, identification and growth of viruses that can be used as vectors and/or vaccines. Thus, the ability to cultivate cells in vitro is not only important for the study of cell physiology, but is also necessary for the production of useful substances that may not otherwise be obtained by cost-effective means.

Among the various cell types that have been grown using in vitro cell culture media, of particular interest are cells derived from the epithelium. The epithelium lines the internal and external surfaces of the organs and glands of higher organisms. Because of this localization at the external interface between the environment and the organism (e.g., the skin) or at the internal interface between an organ and the interstitial space (e.g., the intestinal mucosal lining), the epithelium has a major role in the maintenance of homeostasis. The epithelium carries out this function, for example, by regulating transport and permeability of nutrients and wastes (Freshney, R. I., in: Culture of Epithelial Cells, Freshney, R. I., ed., New York: Wiley-Liss, pp. 1-23 (1992)).

The cells making up the epithelium are generically termed epithelial cells. These cells can be present in multiple layers as in the skin, or in a single layer as in the lung alveoli. As might be expected, the structure, function and physiology of epithelial cells are often tissue-specific. For example, the epidermal epithelial cells of the skin are organized as stratified squamous epithelium and are primarily involved in forming a protective barrier for the organism, while the secretory epithelial cells of many glands are often found in single layers of cuboidal cells that have a major role in producing secretory proteins and glycoproteins. Regardless of their location or function, however, epithelial cells are usually regenerative. That is, under normal conditions, or in response to injury or other activating stimulus, epithelial cells are capable of dividing or growing. This regenerative capacity has facilitated the in vitro manipulation of epithelial cells, to the point where a variety of primary epithelial cells and cell lines have been successfully cultivated in vitro (Freshney, Id.).

While the isolation and use of a variety of epithelial cells and epithelial cell lines have been reported in the literature, the human embryonic kidney cell line 293 ("293 cells"), which exhibits epithelial morphology, has proven particularly useful for studies of the expression of exogenous ligand receptors, production of viruses and expression of allogeneic and xenogeneic recombinant proteins. For example, U.S. Pat. No. 5,166,066 describes the construction of a stable 293 cell line comprising functional GABA receptors that include a benzodiazepine binding site that have proven useful in identification and screening of candidate psychoactive drugs. 293 cells have also been used to produce viruses such as natural and recombinant adenoviruses (Gamier, A., et al., Cytotechnol. 15:145-155 (1994); Bout, A., et al., Cancer Gene Therapy 3(6):S24, abs. P-52 (1996); Wang, J.-W., et al., Cancer Gene Therapy 3(6):S24, abs. P-53 (1996)), which can be used for vaccine production or construction of adenovirus vectors for recombinant protein expression. Finally, 293 cells have proven useful in large-scale production of a variety of recombinant human proteins (Berg, D. T., et al., BioTechniques 14(6):972-978 (1993); Peshwa, M. V., et al., Biotechnol. Bioeng. 41:179-187 (1993); Gamier, A., et al., Cytotechnol. 15:145-155 (1994)).

Cells loosely called fibroblasts have been isolated from many different tissues and are understood to be connective tissue cells. It is clearly possible to cultivate cell lines, loosely termed fibroblastic cells, from embryonic and adult tissues. Fibroblasts characteristically have a "spindle" appearance. Fibroblast-like cells have morphological characteristics typical of fibroblast cells. Under a light microscope the cells appear pointed and elongated ("spindle shaped") when they grow as a monolayer on the surface of a culture vessel. Cell lines can be regarded as fibroblast or fibroblast-like after confirmation with appropriate markers, such as collagen, type I ((Freshney, R. I., in: Culture of Epithelial Cells, Freshney, R. I., ed., New York: Wiley-Liss, pp. 1-23 (1987)).

CHO cells have been classified as both epithelial and fibroblast cells derived from the Chinese hamster ovary. A cell line started from Chinese hamster ovary (CHO-K1) (Kao, F.-T. And Puck, T. T., Proc. Natl. Acad. Sci. USA 60:1275-1281 (1968) has been in culture for many years but its identity is still not confirmed.

Most primary mammalian epithelial cells, mammalian fibroblast cells, epithelial cell lines, and fibroblast cell lines are typically grown in monolayer culture. For some applications, however, it would be advantageous to cultivate such cells as suspension cultures. For example, suspension cultures grow in a three-dimensional space. Monolayer cultures in similar-sized vessels, however, can only grow two-dimensionally on the vessel surface. Thus, suspension cultures can result in higher cell yields and, correspondingly, higher yields of biologicals (e.g., viruses, recombinant polypeptides, etc.) compared to monolayer cultures. In addition, suspension cultures are often easier to feed and scale-up, via simple addition of fresh culture media (dilution subculturing) to the culture vessel rather than trypsinization and centrifugation as is often required with monolayer cultures. The ease of feeding and the ease with which suspension cultures can be scaled up represent a substantial saving in time and labor for handling a comparable number of cells.

Many anchorage-dependent cells, such as primary epithelial cells, primary fibroblast cells, epithelial cell lines, and fibroblast cell lines, however, are not easily adapted to suspension culture. Since they are typically dependent upon anchorage to a substrate for optimal growth, growth of these cells in suspension can require their attachment to microcarriers such as latex or collagen beads. Thus, cells grown in this fashion, while capable of higher density culture than traditional monolayer cultures, are still technically attached to a surface; subculturing of these cells therefore requires similar steps as those used for the subculturing of monolayer cultures. Furthermore, when large batch or fermenter cultures are established, a large volume of microcarriers often settles to the bottom of the culture vessel, thereby requiring a more complicated agitation mechanism to keep the microcarriers (and thus, the cells) in suspension without causing shear damage to the cells (Peshwa, M. V., et al., Biotechnol. Bioeng. 41:179-187 (1993)).

Although many transformed cells are capable of being grown in suspension (Freshney, R. I., Culture of Animal Cells: A Manual of Basic Technique, New York: Alan R. Liss, Inc., pp. 123-125 (1983)), successful suspension cultures often require relatively high-protein media or supplementation of the media with serum or serum components (such as the attachment factors fibronectin and/or vitronectin), or sophisticated perfusion culture control systems (Kyung, Y.-S., et al., Cytotechnol. 14:183-190 (1994)), which can be disadvantageous. In addition, many epithelial cells when grown in suspension form aggregates or "clumps" which can interfere with successful subculturing and reduce growth rate and production of biologicals by the cultures. When clumping occurs, the overall cellular surface area exposed to medium is decreased and the cells are deprived of nutrition and are unable to efficiently exchange waste into the medium. As a result, growth slows, diminished cell densities are obtained, and protein expression is compromised.

Typically, cell culture media formulations are supplemented with a range of additives, including undefined components such as fetal bovine serum (FBS) (5-20% v/v) or extracts from animal embryos, organs or glands (0.5-10% v/v). While FBS is the most commonly applied supplement in animal cell culture media, other serum sources are also routinely used, including newborn calf, horse and human. Organs or glands that have been used to prepare extracts for the supplementation of culture media include submaxillary gland (Cohen, S., J. Biol. Chem. 237:1555-1565 (1961)), pituitary (Peehl, D. M., and Ham, R. G., In Vitro 16:516-525 (1980); U.S. Pat. No. 4,673,649), hypothalamus (Maciag, T., et al., Proc. Natl. Acad. Sci. USA 76:5674-5678 (1979); Gilchrest, B. A., et al., J. Cell Physiol. 120:377-383 (1984)), ocular retina (Barretault, D., et al., Differentiation 18:29-42 (1981)) and brain (Maciag, T., et al., Science 211:1452-1454 (1981)). These types of chemically undefined supplements serve several useful functions in cell culture media (Lambert, K. J. et al., In: Animal Cell Biotechnology, Vol. 1, Spier, R. E. et al., Eds., Academic Press New York, pp. 85-122 (1985)). For example, these supplements provide carriers or chelators for labile or water-insoluble nutrients; bind and neutralize toxic moieties; provide hormones and growth factors, protease inhibitors and essential, often unidentified or undefined low molecular weight nutrients; and protect cells from physical stress and damage. Thus, serum or organ/gland extracts are commonly used as relatively low-cost supplements to provide an optimal culture medium for the cultivation of animal cells.

Unfortunately, the use of serum or organ/gland extracts in tissue culture applications has several drawbacks (Lambert, K. J. et al., In: Animal Cell Biotechnology, Vol. 1, Spier, R. E. et al., Eds., Academic Press New York, pp. 85-122 (1985)). For example, the chemical compositions of these supplements and sera vary between lots, even from a single manufacturer. The supplements can also be contaminated with infectious agents (e.g., mycoplasma and viruses) which can seriously undermine the health of the cultured cells and the quality of the final product. The use of undefined components such as serum or animal extracts also prevents the true definition and elucidation of the nutritional and hormonal requirements of the cultured cells, thus eliminating the ability to study, in a controlled way, the effect of specific growth factors or nutrients on cell growth and differentiation in culture. Moreover, undefined supplements prevent the researcher from studying aberrant growth and differentiation and the disease-related changes in cultured cells. Finally and most importantly to those employing cell culture media in the industrial production of biological substances, serum and organ/gland extract supplementation of culture media can complicate and increase the costs of the purification of the desired substances from the culture media due to nonspecific co-purification of serum or extract proteins.

Improved levels of recombinant protein expression are obtained from cells grown in serum-free medium, relative to the level of expression seen in cells grown in medium supplemented with serum (Battista, P. J. et al., Am. Biotech. Lab. 12:64-68 (1994)). However, serum-free media can still contain one or more of a variety of animal-derived components, including albumin, fetuin, various hormones and other proteins. The presence of proteins or peptides makes purification of recombinant protein difficult, time-consuming, and expensive.

To overcome these drawbacks of the use of serum or organ/gland extracts, a number of so-called "defined" media have been developed. These media, which often are specifically formulated to support the culture of a single cell type, contain no undefined supplements and instead incorporate defined quantities of purified growth factors, proteins, lipoproteins and other substances usually provided by the serum or extract supplement. Since the components (and concentrations thereof) in such culture media are precisely known, these media are generally referred to as "defined culture media." Sometimes used interchangeably with "defined culture media" is the term "serum-free media" or "SFM." A number of SFM formulations are commercially available, such as those designed to support the culture of endothelial cells, keratinocytes, monocytes/macrophages, lymphocytes, hematopoietic stem cells, fibroblasts, chondrocytes or hepatocytes which are available from Life Technologies Corporation, Carlsbad, Calif. The distinction between SFM and defined media, however, is that SFM are media devoid of serum and protein fractions (e.g., serum albumin), but not necessarily of other undefined components such as organ/gland extracts. Indeed, several SFM that have been reported or that are available commercially contain such undefined components, including several formulations supporting in vitro culture of keratinocytes (Boyce, S. T., and Ham, R. G., J. Invest. Dermatol. 81:33 (1983); Wille, J. J., et al., J. Cell. Physiol. 121:31 (1984); Pittelkow, M. R., and Scott, R. E., Mayo Clin. Proc. 61:771 (1986); Pirisi, L., et al., J. Virol. 61:1061 (1987); Shipley, G. D., and Pittelkow, M. R., Arch. DermatoL 123:1541 (1987); Shipley, G. D., et al., J. Cell. Physiol. 138:511-518 (1989); Daley, J. P., et al., FOCUS (GIBCO/LTI) 12:68 (1990); U.S. Pat. Nos. 4,673,649 and 4,940,666). SFM thus cannot be considered to be defined media in the true definition of the term.

Defined media generally provide several distinct advantages to the user. For example, the use of defined media facilitates the investigation of the effects of a specific growth factor or other medium component on cellular physiology, which can be masked when the cells are cultivated in serum- or extract-containing media. In addition, defined media typically contain much lower quantities of protein (indeed, defined media are often termed "low protein media") than those containing serum or extracts, rendering purification of biological substances produced by cells cultured in defined media far simpler and less expensive.

Some extremely simple defined media, which consist essentially of vitamins, amino acids, organic and inorganic salts and buffers have been used for cell culture. Such media (often called "basal media"), however, are usually seriously deficient in the nutritional content required by most animal cells. Accordingly, most defined media incorporate into the basal media additional components to make the media more nutritionally complex, but to maintain the serum-free and low protein content of the media. Examples of such components include bovine serum albumin (BSA) or human serum albumin (HSA); certain growth factors derived from natural (animal) or recombinant sources such as epidermal growth factor (EGF) or fibroblast growth factor (FGF); lipids such as fatty acids, sterols and phospholipids; lipid derivatives and complexes such as phosphoethanolamine, ethanolamine and lipoproteins; protein and steroid hormones such as insulin, hydrocortisone and progesterone; nucleotide precursors; and certain trace elements (reviewed by Waymouth, C., in: Cell Culture Methods for Molecular and Cell Biology, Vol. 1: Methods for Preparation of Media, Supplements, and Substrata for Serum-Free Animal Cell Culture, Barnes, D. W., et al., eds., New York: Alan R. Liss, Inc., pp. 23-68 (1984), and by Gospodarowicz, D., Id., at pp 69-86 (1984)).

The use of animal protein supplements in cell culture media, however, also has certain drawbacks. For example, there is a risk that the culture medium and/or products purified from it can be immunogenic, particularly if the supplements are derived from an animal different from the source of the cells to be cultured. If biological substances to be used as therapeutics are purified from such culture media, certain amounts of these immunogenic proteins or peptides can be co-purified and can induce an immunological reaction, up to and including anaphylaxis, in an animal receiving such therapeutics.

To obviate this potential problem, supplements derived from the same species as the cells to be cultured can be used. For example, culture of human cells can be facilitated using HSA as a supplement, while media for the culture of bovine cells would instead use BSA. This approach, however, runs the risks of introducing contaminants and adventitious pathogens into the culture medium (such as Creutzfeld-Jakob Disease (CJD) from HSA preparations, or Bovine Spongiform Encephalopathy ("Mad Cow Disease") prion from BSA preparations), which can obviously negatively impact the use of such media in the preparation of animal and human therapeutics. In fact, for such safety reasons, the biotechnology industry and government agencies are increasingly regulating, discouraging and even forbidding the use of cell culture media containing animal-derived proteins which can contain such pathogens.

To overcome the limitations of the use of animal proteins in SFM, several attempts have been made to construct animal cell culture media that are completely free of animal proteins. For example, some culture media have incorporated extracts of yeast cells into the basal medium (see, for example, U.K. Patent Application No. GB 901673; Keay, L., Biotechnol. Bioengin. 17:745-764 (1975)) to provide sources of nitrogen and other essential nutrients. In another approach, hydrolysates of wheat gluten have been used, with or without addition of yeast extract, to promote in vitro growth of animal cells (Japanese Patent Application No. JP 2-49579). Still other media have been developed in which serum is replaced by enzymatic digests of meat, or of proteins such as α-lactalbumin or casein (e.g., peptone), which have been traditionally used in bacterial culture (Lasfargues, E. Y., et al., In Vitro 8(6):494-500 (1973); Keay, L., Biotechnol. Bioeng. 17:745-764 (1975); Keay, L., Biotechnol. Bioeng. 19:399-411 (1977); Schlager, E.-J., J. Immunol. Meth. 194:191-199 (1996)). None of these approaches, however, provided a culture medium optimal for the cultivation of a variety of animal cells. Moreover, extracts from certain plants, including wheat, barley, rye and oats have been shown to inhibit protein synthesis in cell-free systems derived from animal cells (Coleman, W. H., and Roberts, W. K., Biochim. Biophys. Acta 696:239-244 (1982)), suggesting that the use of peptides derived from these plants in cell culture media can actually inhibit, rather than stimulate, the growth of animal cells in vitro. More recently, animal cell culture SFM formulations comprising rice peptides have been described and shown to be useful in cultivation of a variety of normal and transformed animal cells (see U.S. Pat. No. 6,103,529, incorporated herein by reference in its entirety).

Notwithstanding the potential difficulties posed by the addition of animal derived supplements to cell culture media, such supplements are in routine use. One such supplement that is frequently added to defined media is transferrin. Transferrin functions in vivo to deliver iron to cells. The mechanism of iron uptake by mammalian cells has been reviewed (Qian, Z. M. and Tang, P. L. (1995) Biochim.

Biophys. Acta 1269, 205-214). As iron is required as a co-factor in numerous metabolic processes including energy generation and oxidative respiration, serum-free media are often supplemented with transferrin in order to deliver the requisite iron for the successful cultivation of most cells in vitro. Concern about various potential adventitious agents in preparations of transferrin has stimulated a search for other natural iron carrier compounds which can be used as a substitute for transferrin. This search is complicated by the fact that the natural iron carriers are often derived from serum and thus are subject to the above-described limitations of serum supplementation.

To overcome the limitations of using naturally derived metal carriers, certain metal binding compounds are being explored for use in supplying metals, particularly zinc, iron, manganese and magnesium, to cultured cells. Simple carriers such as chelating agents (e.g., EDTA) and certain acids or salts thereof (e.g., citrate, picolinate, and derivatives of benzoic acid or hydroxamic acid) have been shown to be useful in certain serum-free growth media (see U.S. Pat. Nos. 5,045,454 and 5,118,513; Testa et al., Brit. J. Haematol. 60:491-502, (1985); Ganeshaguru et al., Biochem. Pharmacol. 29:1275-1279 (1980); White et al., Blood 48:923-929 (1976)).

Although these references disclose some metal carriers, the interpretation of the data is complicated by several experimental factors. The data were gathered from a limited number of cell lines and show results of a single passage. In addition, the media were supplemented with serum. Serum inherently contains transferrin and other potential iron carriers. There is a "carry-over effect" on growth of cells which have been cultured in serum-supplemented medium, even after one or two passages in the absence of serum or transferrin (see, for example, Keenan, J. and Clynes, M. (1996) In Vitro Cell Dev. Biol-Animal 32, 451-453). Other known metal binding compounds have been used medicinally to remove iron from the body and not for delivery. Unfortunately, many of these simple iron chelating compounds do not provide sufficient iron availability to, or uptake by, cultured cells.

Once a suitable medium formulation for the growth of a particular cell type has been determined, it is frequently necessary to alter the cell in question so as to optimize the production of a desired biological substance. A critical step in the effective production and purification of biological substances is the introduction of one or more macromolecules (e.g., peptides, proteins, nucleic acids, etc.) into the cell in which the material will be produced. This can be accomplished by a variety of methods. One widely used method to introduce macromolecules into a cell is known as transfection.

Typically, the target cell is grown to a desired cell density in a cell culture medium optimized for growth of the cell. Once the desired density is reached, the medium is exchanged for a medium optimized for the transfection process. Under most circumstances, the medium used for transfection does not support the growth of the cells but the transfection medium is merely used for the purpose of introducing nucleic acids into the cells. As a result, the process generally requires collecting the cells from the culture, usually by centrifugation, washing the cells to remove traces of the growth medium, suspending the cells in a transfection medium in the presence of the macromolecule of interest, incubating the cells in the transfection medium for a period of time sufficient for the uptake of the macromolecule, optionally, removing the transfection medium and washing the remnants of the transfection medium from the cells and then re-suspending the transfected cells in a growth medium. The steps of exchanging the growth media for transfection media, washing the cells, and exchanging the transfection media back to a growth media require a great deal of hands-on manipulation of the cells thereby adding substantially to the time and expense of recombinant DNA technology.

As an historical example, 293 cells have been cultivated in monolayer cultures in a serum-supplemented version of a complex medium (i.e., DMEM). When grown in suspension, 293 cells have a tendency to aggregate into large clusters of cells. The formation of these large cell aggregates reduces the viability of the cells. Since the cells in the center of the aggregates are not directly exposed to the medium, these cells have limited access to nutrients in the medium and have difficulty in exchanging waste into the medium. In addition, this reduced access to the medium makes cells in clusters unsuitable for genetic manipulation by factors introduced into the medium (i.e., for transformation by nucleic acids). As a result of these difficulties, 293 cells have not generally been used in suspension culture for the production of biological materials.

Thus, there still remains a need in the art for a cell medium and transient transfection system that permits the growth of eukaryotic cells in suspension while permitting the transfection of the cells with a reduced amount of manipulation. Such a medium should preferably be a serum-free and/or chemically defined and/or protein-free medium and/or a medium lacking animal derived materials which facilitates the growth of mammalian cells to high density and/or increases the level of expression of recombinant protein, reduces cell clumping, and which does not require supplementation with animal proteins, such as serum, transferrin, insulin and the like. Preferably a medium of this type will permit the suspension cultivation of mammalian cells that are normally anchorage-dependent, including epithelial cells and fibroblast cells, such as 293 cells and CHO cells. Preferably, such a medium would also enable cultivation and culturing of the aforementioned cell types at higher density than can be typically obtained with currently available media. Additionally, such culture media will allow easier and more cost-effective and efficient production and purification of high quantities of commercially or scientifically important biological substances (e.g., viruses, recombinant proteins, biologics, recombinant antibodies, etc.) produced by cultured mammalian cells in the biotechnology industry, and will provide more consistent results in methods employing the cultivation of mammalian cells. These and other needs are met by the present invention.

SUMMARY

The present invention provides a cell culture and transfection system, whereby the system supports introduction by way of transfection and subsequent expression of one or more macromolecules (such as, e.g., expressible nucleic acids) into a plurality of eukaryotic cells in culture, and further supports the cultivation and growth of the cells subsequent to the introduction/transfection, wherein growth of the at least one cell continues in the medium in the absence of the medium being supplemented with fresh medium.

In some embodiments, it is not necessary to remove, replenish or replace the medium used during the introduction/transfection of the cells from the presence of the cells to support the further growth thereof. In another preferred embodiment, after the introduction/transfection, growth of the cells and production of an expressed protein from the expressible nucleic acid can be accomplished in a volume of medium that is about the same volume up to no more than about 10 times the volume of the medium in which the introduction/transfection occurred. Using the medium of the present invention, it is not necessary to replenish, replace or supplement the medium after one has introduced nucleic acid into cells, and before cells into which nucleic acid has been introduced are further cultured to express the nucleic acid.

Transient expression is fast becoming the system of choice for rapid mammalian protein production. The flexibility of transient transfection enables a rapid realization time from concept to protein-in-hand and many different proteins can be produced simultaneously, or serially. The next key advance in transient transfection technology is to approach or equal expression levels attained using stable expression systems without losing the speed and flexibility of the transient format. We report for the first time the development of a novel transient transfection system that utilizes high density 293F cell cultures to generate expression levels of >1 g/L (up to about 2 g/L) of human IgG and anon-IgG proteins within 7 days after cells are transfected.

To attain such high levels of protein expression, a novel cell culture system which includes a new high density growth culture medium in combination with a population of suspension cells that are adapted for high density growth in such a media was developed that allows certain populations of mammalian cells to reach viable cell densities of up to $20 \times 10^6$ cells/ml (more typically up to about $15 \times 10^6$ cells/ml). These ultra-high density cultures enable transfection at higher cell densities than traditional protocols, significantly increasing the volumetric yield of protein. Additive The addition of one or more expression enhancer formulations following or during transfection was also found to boost protein expression level to levels up to 10- to 12-fold higher than the expression levels seen with current commercially available transient transfection systems. Parental suspension culture mammalian cells were adapted for improved growth and viability characteristics under high density culture conditions, and were then further selected for increased protein production. The resulting high density adapted cells have an increased growth rate, increased cell size, and increased specific productivity compared to the parental cell line. Finally, the transfection method was optimized through the use of one or more transfections reagents that are used in combination with one or more expression enhancer formulations to further increase overall protein yield.

When all of these improvements were combined into a single expression system, protein levels were increased up to 10-fold for both IgG and non-IgG recombinant proteins compared to the commercially available FreeStyle™ 293 expression system and expression levels of >1 g/L were attained for multiple proteins. Additionally, protein functionality was demonstrated to be comparable for several proteins expressed in the high yield expression system of the present invention when compared to the popular commercially available FreeStyle™ 293 system. Together, these results indicate that significant increases in functional protein yields can be attained using a novel transient mammalian expression system that incorporates numerous advances in protein expression technology into a single, easy to use format.

The present invention also provides a method of cultivating eukaryotic cells comprising: (a) contacting the cells with the cell culture medium of the present invention; (b) maintaining the cells under conditions suitable to support cultivation of the cells in culture; and (c) optionally expressing a nucleic acid to form a protein product.

The present invention also provides a method for introducing one or more macromolecules into at least one eukaryotic cell in culture, the method comprising: (a) culturing at least one eukaryotic cell in the medium of claim 1 in culture; (b) introducing at least one macromolecule into the culture under conditions sufficient to cause one or more of the at least one macromolecule to be introduced in the at least one cell; and (c) cultivating the at least one cell in the medium to produce a product whose production is controlled by the at least one molecule, wherein growth of the at least one cell continues in the medium in the absence of the medium being with fresh medium, wherein it is not necessary to remove medium used during the introduction from the presence of the at least one cell to support growth of the at least one cell, and/or wherein after the introduction, growth is accomplished in cultivation in a volume of medium that is about the same volume up to no more than about 10 times the volume of the medium in which the introduction occurred.

The present invention also provides a kit for the cultivation and transfection of cells in vitro, the kit comprising the cell culture medium of the present invention, and optionally further comprising one or more of: one or more agents for the introduction of at least one molecule into a cell, one or more macromolecules, at least one cell, and instructions for culturing the at least one cell in culture and/or for introducing at least one macromolecule into at least one cell in culture.

The present invention also provides a composition comprising the cell culture medium of the present invention and at least one component selected from the group consisting of at least one eukaryotic cell, one or more agents for the introduction of at least one macromolecule into at least one cell, and one or more macromolecules.

Other embodiments of the present invention will be apparent to one of ordinary skill in light of the following drawings and description of the invention, and of the claims.

BRIEF DESCRIPTION OF DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention.

In the drawings:

FIG. 4 shows a comparison of expression levels for 4 different and unique proteins using a high yield transient transfection system in accordance with some embodiments and a prior art transient transfection system (Freestyle™ 293 system).

DETAILED DESCRIPTION OF THE PREFERRED EMBODIMENTS

Figure 1:
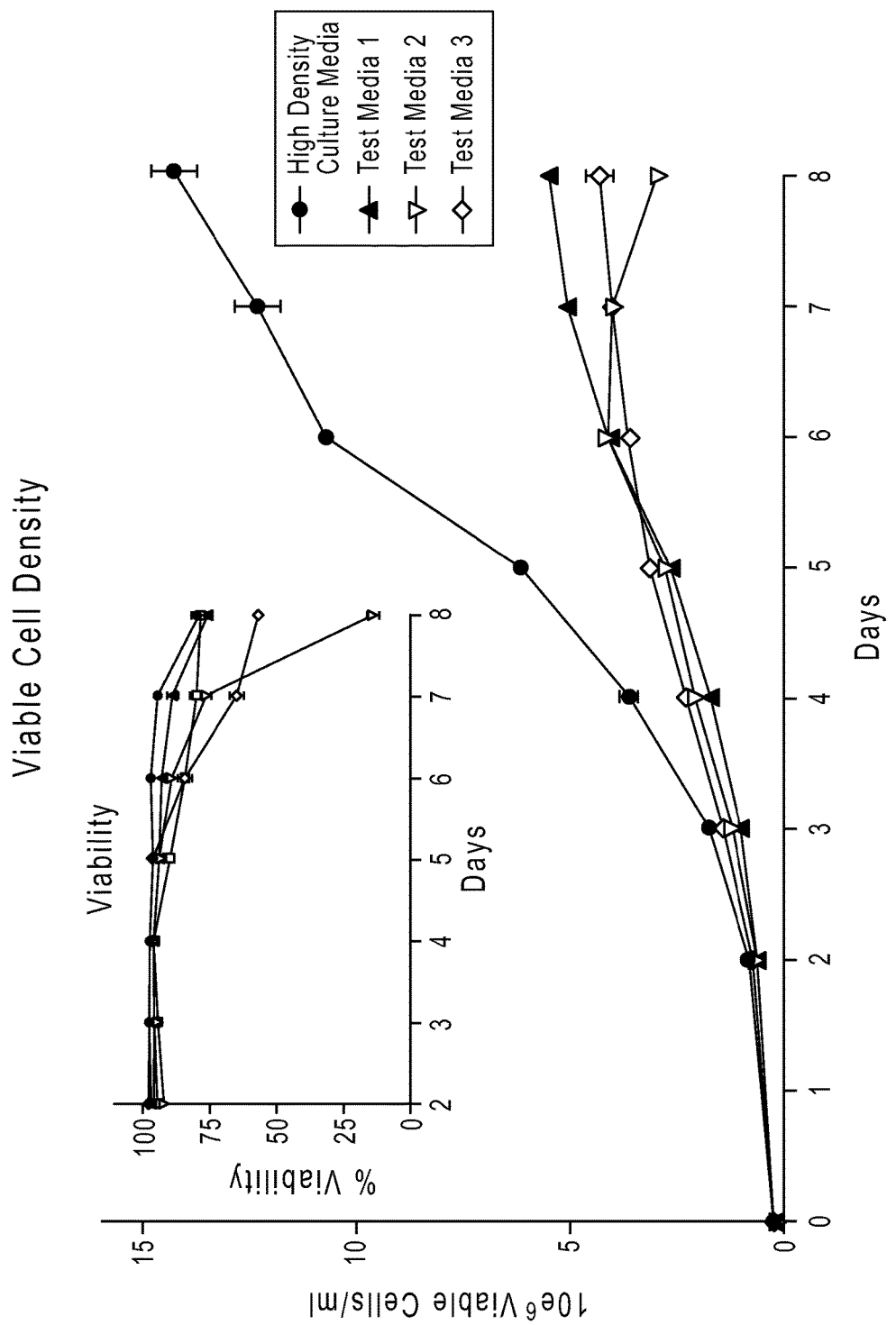
FIG. 1 is a graph demonstrating cell densities that are achievable using the transient transfection system in accordance with some embodiments of the invention. Cell adapted for high density growth were slowly adapted into various media over 3 passages. The media to which the cells were adapted include High Density Culture Media in accordance with one embodiment of the invention (closed circles), Test Media 1 (closed triangles), Test Media 2 (open triangles), Test Media 3 (open diamonds). Cells were cultured for multiple passages in each of the media before being seeded in 30 ml flasks at $0.2 \times 10^6$ cells/ml. Cell density and viability were monitored over 8 days.

The present invention provides improved medium formulations for the growth of both eukaryotic and prokaryotic cells. The inventive media support cell growth, introduction of macromolecules into cells in culture and cell cultivation without requiring replenishment, replacement, supplementation, or changing medium between growth, introduction and/or cultivation. The media of the present invention can be used to support or enhance the growth and cultivation of any cell. The present invention also provides compounds that can be used as substitutes or to replace one or more undesired components, e.g., animal derived components. The replacement compounds provide at least one desired function of the undesired component.

Definitions

In the description that follows, a number of terms used in cell culture and recombinant DNA technology are utilized extensively. In order to provide a clear and more consistent understanding of the specification and claims, including the scope to be given such terms, the following definitions are provided.

The term "introduction" of a macromolecule or compound into culture refers to the provision of the macromolecule or compound into the culture medium.

The term "introduction" of a macromolecule or compound into at least one cell refers to the provision of a macromolecule or compound to a cell, such that the macromolecule or compound becomes internalized in the cell. For example, a macromolecule or compound can be introduced into a cell using transfection, transformation, injection, and/or liposomal introduction, and may also be introduced into a cell using other methods known to those of ordinary skill in the art. Preferably, a macromolecule or compound is introduced into a cell by liposomal introduction. The macromolecule is preferably a protein, peptide, polypeptide, or nucleic acid. The macromolecule may a protein. Alternatively, the macromolecule may be a peptide. Alternatively, the macromolecule may be a polypeptide. The macromolecule may also be a nucleic acid.

The term "macromolecule," as used herein, encompasses biomolecules. In one embodiment, the term macromolecule refers to nucleic acid. In a preferred embodiment, the term macromolecule refers to deoxyribonucleic acid (DNA) and ribonucleic acid (RNA). More preferably, the term macromolecule refers to DNA. More preferably, the term macromolecule refers to complementary DNA (cDNA). A macromolecule can be charged or uncharged. A DNA molecule is an example of a charged macromolecule. In some instances, the term "macromolecule", as used herein, may be used interchangeably with the term "expressible nucleic acid".

The term "transfection" is used herein to mean the delivery of nucleic acid, protein or other macromolecule to a target cell, such that the nucleic acid, protein or other macromolecule is expressed or has a biological function in the cell.

The term "expressible nucleic acid" as used herein includes both DNA and RNA without regard to molecular weight, and the term "expression" means any manifestation of the functional presence of the nucleic acid within the cell including, without limitation, both transient expression and stable expression. Functional aspects include inhibition of expression by oligonucleotides or protein delivery.

The term "expression of nucleic acid" and their equivalents refer to the replication of the nucleic acid in a cell, to transcription of DNA to messenger RNA, to translation of RNA to protein, to post-translational modification of protein, and/or to protein trafficking in the cell, or variations or combinations thereof.

The term "ingredient" refers to any compound, whether of chemical or biological origin, that can be used in cell culture media to maintain or promote the growth or proliferation of cells. The terms "component," "nutrient" and "ingredient" can be used interchangeably and are all meant to refer to such compounds. Typical ingredients that are used in cell culture media include amino acids, salts, metals, sugars, lipids, nucleic acids, hormones, vitamins, fatty acids, proteins and the like. Other ingredients that promote or maintain cultivation of cells ex vivo can be selected by those of skill in the art, in accordance with the particular need. Media of the present invention can include one or more components selected from the group consisting of bovine serum albumin (BSA) or human serum albumin (HSA), a one or more growth factors derived from natural (animal) or recombinant sources such as epidermal growth factor (EGF) or fibroblast growth factor (FGF), one or more lipids, such as fatty acids, sterols and phospholipids, one or more lipid derivatives and complexes, such as phosphoethanolamine, ethanolamine and lipoproteins, one or more proteins, one or more and steroid hormones, such as insulin, hydrocortisone and progesterone, one or more nucleotide precursors; and one or more trace elements.

The term "cell" as used herein refers includes all types of eukaryotic and prokaryotic cells. In preferred embodiments, the term refers to eukaryotic cells, especially mammalian cells. In certain exemplary though non-limiting embodiments, the term "cell" is meant to refer to human 293 cells, or a variant thereof, such as, e.g., a 293 variant that can grow in suspension. Particularly preferred are variants of 293 cells that can grow, proliferate and be transfected in suspension culture, in particular those variants that can be cultured at high density (e.g., greater than about $2\times10^6$ cells/ml, more preferably greater than about $3\times10^6$ cells/ml, or even optionally greater than about $4\times10^6$ cells/ml). An example of such a variant 293 cell line is EXPI293™Fcells. In other exemplary though non-limiting embodiments, the term "cell" is meant to refer to a CHO cell.

As used herein, the term "high density" when used in the context of culturing cells in accordance with the present invention, and of methods of the invention employing same for the purpose of conducting transfection workflows, generally refers to a known cell line, or a variant of a known cell line, that can be grown or cultured in an appropriate cell culture medium to densities of greater than about $1\times10^6$ cells/ml, more preferably greater than about $2\times10^6$ cells/ml, most preferably greater than about $3\times10^6$ cells/ml, or even optionally greater than about $4\times10^6$ cells/ml, or more up to about $20\times10^6$ cells/ml, while still retaining the ability to be transfected at high efficiency and are able to express a target protein at high levels (e.g., levels exceeding 200 g/ml to up to about 1 mg/ml or more.

The phrase "high density culture medium" is used herein to refer to any culture medium capable of sustaining the growth of mammalian cells, preferably cells growing in suspension, at densities of up to about $2\times10^7$ cells/ml while maintaining viability of said cells in excess of about 80% and further, maintaining the ability of said suspension cells to be efficiently transfected and express high amounts of recombinant protein. The "high density culture medium" used in the practice of the present invention may vary between different applications and uses, and may depend on the nature of the cell line being used, the desired protein being transiently expressed, the nature of the transfection modality selected for transfer of the expression vector into cells, and the amount and nature of any expression enhancers added to the system as described below. Nevertheless, preferred "high density culture medium" contemplated for use in the present transient expression systems and methods will typically be serum-free, protein-free, allow the cultivation and growth of suspension cells to a density of up to about $2\times10^7$ cells/ml, more typically between about $2\times10^6$ cells/ml to about $1\times10^7$ cells/ml, and will further enable the yield of protein produced in the transient expression system to exceed at least 200 µg/mL of cell culture up to 2 mg/mL of cell culture, more typically between about 500 µg/ml of cell culture to about 1 mg/mL of cell culture. Ideally, the high density culture medium used in accordance with the present invention will facilitate the transfection of cells at densities in the range of about $1\times10^6$ to about $20\times10^6$ cells/ml, about $2\times10^6$ to about $2\times10^6$ cells/ml, or about $2.5\times10^6$ to about $6\times10^6$ cells/ml. Exemplary high density culture media suitable for use in the practice of the present invention include, though are not limited to, HuMEC Basal Serum free Medium, KNOCKOUT™ CTS™ XenoFREE ESC/iPSC Medium, STEMPRO™-34 SFM Medium, STEMPRO™ NSC Medium, ESSENTIAL™-8 Medium, Medium 254, Medium, 106, Medium, 131, Medium, 154, Medium, 171, Medium 171, Medium 200, Medium 231, HeptoZYME-SFM, Human Endothelial-SFM, GIBCO® FREESTYLE™ 293 Expression Medium, Medium 154CF/PRF, Medium 154C, Medium 154 CF, Medium 106, Medium 200PRF, Medium 131, Essential™-6 Medium, STEMPRO™-34 Medium, Gibco® Astrocyte Medium, AIM V® Medium CTS™, AMINOMAX™ C-100 Basal Medium, AMINOMAX™-II Complete Medium, CD FORTICHO™ Medium, CD CHO AGT Medium, CHO-S-SFM Medium, GIBCO®FREESTYLE™ CHO Expression Medium, CD OPTICHO™ Medium, CD CHO Medium, CD DG44 Medium, SF-900™ Medium, EXPI293™ Expression Medium, LHC Basal Medium, LHC-8 Medium, 293 SFM Medium, CD 293 Medium, AEM Growth Medium, PER.C6® Cell Medium, AIM V® Medium, EXPILIFE® Medium, Keratinocyte-SFM Medium, LHC Medium, LHC-8 Medium, LHC-9 Medium, and any derivatives or modifications thereof. In certain preferred though non-limiting embodiments, a high density culture media may be CD FORTICHO™ Medium, CD CHO AGT Medium, CHO-S-SFM Medium, GIBCO®FREESTYLE™ CHO Expression Medium, CD OPTICHO™ Medium, CD CHO Medium, CD DG44 Medium, GIBCO® FREESTYLE™ 293 Expression Medium, EXPI293™ Expression Medium, or a like medium, or a modified version thereof. The above listed exemplary high density culture media may be particularly suitable for the high density growth, propagation, transfection and maintenance of CHO cells, a CHO cell variant, 293 cells, a 293 cell variant, CapT cells, a CapT cell variant, or any other cells adapted for use in a high density culture system.

The phrase "cells adapted for high density culture" is meant to refer to a cell lineage or a (non-clonal) population of cells derived from the same parental cell lineage that has been adapted to grow at high density in a high-density culture medium while retaining cell viability at or above about 80%. Such cells may be isolated or selected out from the parental population of cells by maintaining the cells at high density over >40, >50, >60, >70, or >80 sequential passages and gradually replacing the proportion of growth medium with the desired high-density culture medium. Optionally, during the process, different pools of cells may be individually propagated and subjected to the selection procedure while simultaneously assessing transfection efficiency and or protein expression efficiency, so that non-clonal population of cells may be selected that can be sustained and grown at high density, transfected with high efficiency, and express high levels of a desired recombinant protein. While it will be readily apparent to the skilled practitioner that a variety of cell types and lineages may be subjected to this selection procedure, it has been determined that cell lineages derived from CHO cells, cell lineages derived from 293 fibroblast cells, and cells derived from CapT cells are particularly amenable to the selection process for being adapted to high density growth conditions. Ideally, cells that are adapted to high density growth culture and amenable for use in the present invention will also be capable of being transfected at high efficiency and/or capable of expressing recombinant protein at yield exceeding at least 200 about µg/mL of cell culture up to about 2 mg/mL of cell culture, more typically between about 500 µg/ml of cell culture to about 1 mg/mL of cell culture. Ideally, cells adapted for high density culture used in accordance with the present invention are capable of being sustained and transfected at densities in the range of about $1\times10^6$ to about $20\times10^6$ cells/ml, about $2\times10^6$ to about $2\times10^6$ cells/ml, or about $2.5\times10^6$ to about $6\times10^6$ cells/ml.

By "cell culture" or "culture" is meant the maintenance of cells in an artificial, in vitro environment.

By "cultivation" is meant the maintenance of cells in vitro under conditions favoring growth and/or differentiation and/or or continued viability. "Cultivation" can be used interchangeably with "cell culture." Cultivation is assessed by number of viable cells/ml culture medium. Cultivation after introduction of a macromolecule preferably includes production of a product, for example, a protein product on a virus.

The term "replenishing, replacing, or supplementing medium" as used herein refers to adding a volume of fresh cell culture medium to medium that was already present in culture and/or replacing medium that was already present in culture with fresh medium, and/or supplementing medium already present in culture with new medium. Fresh medium is medium that does not contain the one or more macromolecules or compounds to be introduced into at least one cell or medium that has not been in contact with cells to support their growth on cultivation. The skilled artisan can determine whether there is an advantage from or a need to remove and/or replenish, replace or supplement medium by monitoring cell growth and/or viability by techniques known in the art, such as cell counting (manual or automated), trypan blue exclusion, production of protein or other substance, alamar blue assay, presence or concentration of one or more metabolic products, cell adhesion, morphological appearance, analysis of spent medium, etc. One or a combination of monitoring techniques can be used to determine whether the medium needs to be to support growth, introduction of at least one macromolecule and/or cultivation after introduction of at least one macromolecule.

"Recombinant protein" refers to protein that is encoded by a nucleic acid that is introduced into a host cell. The host cell expresses the nucleic acid. The term "expressing a nucleic acid" is synonymous with "expressing a protein from an RNA encoded by a nucleic acid. "Protein" as used herein broadly refers to polymerized amino acids, e.g., peptides, polypeptides, proteins, lipoproteins, glycoproteins, etc.

The term "protein yield" refers to the amount of protein expressed by cultured cells, and can be measured, for example, in terms of grams of protein produced/ml medium. If the protein is not secreted by the cells, the protein can be isolated from the interior of the cells by methods known to those of ordinary skill in the art. If the protein is secreted by the cells, the protein can be isolated from the culture medium by methods known to those of ordinary skill in the art. The amount of protein expressed by the cell can readily be determined by those of ordinary skill in the art. The protein may be a recombinant protein.

A "protein product" is a product associated with production or an action by a protein. A protein product may be a protein. A protein product may also be a product resulting from action of a protein by one or more other substances to produce a product. An example of such action is enzymatic action by a protein.

By "suspension culture" is meant cell culture in which the majority or all of cells in a culture vessel are present in suspension, and the minority or none of the cells in the culture vessel are attached to the vessel surface or to another surface within the vessel. Preferably, "suspension culture" has greater than 75% of the cells in the culture vessel are in suspension, not attached to a surface on or in the culture vessel. More preferably, a "suspension culture" has greater than 85% of the cells in the culture vessel are present in suspension, not attached to a surface on or in the culture vessel. Even more preferred is a "suspension culture" with greater than 95% of the cells in the culture vessel present in suspension, not attached to a surface on or in the culture vessel.

The medium, methods, kit and composition of the present invention are suitable for either monolayer or suspension culture, transfection, and cultivation of cells, and for expression of protein in cells in monolayer or suspension culture. Preferably, the medium, methods, kit and composition of the present invention are for suspension culture, transfection, and cultivation of cells, and for expression of protein product in cells in suspension culture.

By "culture vessel" is meant any container, for example, a glass, plastic, or metal container, that can provide an aseptic environment for culturing cells.

The phrases "cell culture medium," "tissue culture medium," "culture medium" (plural "media" in each case) and "medium formulation" refer to a nutritive solution for cultivating cells or tissues. These phrases can be used interchangeably.

The term "combining" refers to the mixing or admixing of ingredients.

Derivative of a molecule includes some compounds that comprise the base molecule, but have additional or modified side groups. Preferably, a "derivative" can be formed by reacting the base molecule with only 1, but possibly 2, 3, 4, 5, 6, etc. reactant molecules. A single step reaction is preferred, but multi-step, e.g., 2, 3, 4, 5, 6, etc. reactions are known in the art to form derivatives. Substitution, condensation and hydrolysis reactions are preferred and may be combined to form the derivative compound. Alternatively, a derivative compound may be a compound that preferably in 1, but possibly 2, 3, 4, 5, 6, etc. reactions can form the base compound or a substitution or condensation product thereto.

A cell culture medium is composed of a number of ingredients and these ingredients can vary from medium to medium. Each ingredient used in a cell culture medium has its unique physical and chemical characteristics. Compatibility and stability of ingredients are determined in part by the "solubility" of the ingredients in aqueous solution. The terms "solubility" and "soluble" refer to the ability of an ingredient to form and remain in solution with other ingredients. Ingredients are thus compatible if they can be maintained in solution without forming a measurable or detectable precipitate.

By "compatible ingredients" is also meant those media components which can be maintained together in solution and form a "stable" combination. A solution containing "compatible ingredients" is said to be "stable" when the ingredients do not precipitate, degrade or decompose substantially such that the concentration of one or more of the components available to the cells from the media is reduced to a level that no longer supports the optimum or desired growth of the cells. Ingredients are also considered "stable" if degradation cannot be detected or when degradation occurs at a slower rate when compared to decomposition of the same ingredient in a 1× cell culture media formulation. For example, in 1× media formulations glutamine is known to degrade into pyrolidone carboxylic acid and ammonia. Glutamine in combination with divalent cations are considered "compatible ingredients" since little or no decomposition of the glutamine can be detected over time in solutions or combinations in which both glutamine and divalent cations are present. See U.S. Pat. No. 5,474,931. Thus, the term "compatible ingredients" as used herein refers to the combination of particular culture media ingredients which, when mixed in solution either as concentrated or 1× formulations, are "stable" and "soluble."

The term "1× formulation" is meant to refer to any aqueous solution that contains some or all ingredients found in a cell culture medium at working concentrations. The "1× formulation" can refer to, for example, the cell culture medium or to any subgroup of ingredients for that medium. The concentration of an ingredient in a 1× solution is about the same as the concentration of that ingredient found in a cell culture formulation used for maintaining or cultivating cells in vitro. A cell culture medium used for the in vitro cultivation of cells is a 1× formulation by definition. When a number of ingredients are present, each ingredient in a 1× formulation has a concentration about equal to the concentration of each respective ingredient in a medium during cell culturing. For example, RPMI-1640 culture medium contains, among other ingredients, 0.2 g/L L-arginine, 0.05 g/L L-asparagine, and 0.02 g/L L-aspartic acid. A "1× formulation" of these amino acids contains about the same concentrations of these ingredients in solution. Thus, when referring to a "1× formulation," it is intended that each ingredient in solution has the same or about the same concentration as that found in the cell culture medium being described. The concentrations of ingredients in a 1× formulation of cell culture medium are well known to those of ordinary skill in the art. See, for example, Methods For Preparation of Media, Supplements and Substrate For Serum-Free Animal Cell Culture Allen R. Liss, N.Y. (1984), Handbook of Microbiological Media, Second Ed., Ronald M. Atlas, ed. Lawrence C. Parks (1997) CRC Press, Boca Raton, Fla. and Plant Culture Media, Vol. 1: Formulations and Uses E. F. George, D. J. M. Puttock, and H. J. George (1987) Exegetics Ltd. Edington, Westbury, Wilts, BA13 4QG England each of which is incorporated by reference herein in its entirety. The osmolarity and/or pH, however, can differ in a 1× formulation compared to the culture medium, particularly when fewer ingredients are contained in the 1× formulation.

A "10× formulation" is meant to refer to a solution wherein the concentration of each ingredient in that solution is about 10 times more than the concentration of each respective ingredient in a medium during cell culturing. For example, a 10× formulation of RPMI-1640 culture medium can contain, among other ingredients, 2.0 g/L L-arginine, 0.5 g/L L-asparagine, and 0.2 g/L L-aspartic acid (compare 1× formulation, above). A "10× formulation" can contain a number of additional ingredients at a concentration about 10 times that found in the 1× culture formulation. As will be readily apparent, "25× formulation," "50× formulation," "100× formulation," "500× formulation," and "1000× formulation" designate solutions that contain ingredients at about 25-, 50-, 100-, 500-, or 1000-fold concentrations, respectively, as compared to a 1× cell culture formulation. Again, the osmolarity and pH of the medium formulation and concentrated solution can vary.

The term "trace element" or "trace element moiety" refers to a moiety which is present in a cell culture medium in only very low (i.e., "trace") amounts or concentrations, relative to the amounts or concentrations of other moieties or components present in the culture medium. In the present invention, these terms encompass $Ag^+$, $Al^{3+}$, $Ba^{2+}$, $Cd^{2+}$, $Co^{2+}$, $Cr^{3+}$, $Cu^{1+}$, $Cu^{2+}$, $Fe^{2+}$, $Fe^{3+}$, $Ge^{4+}$, $Se^{4+}$, $Br^-$, $I^-$, $Mn^{2+}$, $F^-$, $Si^{4+}$, $V^{5+}$, $Mo^{6+}$, $Ni^{2+}$, $Rb^+$, $Sn^{2+}$ and $Zr^{4+}$ and salts thereof. For example, the following salts can be used as trace elements in the culture media of the invention: $AgNO_3$, $AlCl_3 \cdot 6H_2O$, $Ba(C_2H_3O_2)_2$, $CdSO_4 \cdot 8H_2O$, $CoCl_2 \cdot 6H_2O$, $Cr_2(SO_4)_3 \cdot 1H_2O$, $GeO_2$, $Na_2SeO_3$, $H_2SeO_3$, KBr, KI, $MnCl_2 \cdot 4H_2O$, NaF, $Na_2SiO_3 \cdot 9H_2O$, $NaVO_3$, $(NH_4)_6Mo_7O_{24} \cdot 4H_2O$, $NiSO_4 \cdot 6H_2O$, RbCl, $SnCl_2$, and $ZrOCl_2 \cdot 8H_2O$. Suitable concentrations of trace element moieties can be determined by one of ordinary skill in the art using only routine experimentation.

The term "amino acid" refers to amino acids or their derivatives (e.g., amino acid analogs), as well as their D- and L-forms. Examples of such amino acids include glycine, L-alanine, L-asparagine, L-cysteine, L-aspartic acid, L-glutamic acid, L-phenylalanine, L-histidine, L-isoleucine, L-lysine, L-leucine, L-glutamine, L-arginine, L-methionine, L-proline, L-hydroxyproline, L-serine, L-threonine, L-tryptophan, L-tyrosine, and L-valine, N-acetyl cysteine.

A "chemically defined" medium is one in which each chemical species and its respective quantity is known prior to its use in culturing cells. A chemically defined medium is made without lysates or hydrolysates whose chemical species are not known and/or quantified. A chemically defined medium is one preferred embodiment of the medium of the present invention.

The terms "serum-free culture conditions" and "serum-free conditions" refer to cell culture conditions that exclude serum of any type. These terms can be used interchangeably.

A "serum-free medium" (sometimes referred to as "SFM Medium") is a medium that contains no serum (e.g., fetal bovine serum (FBS), calf serum, horse serum, goat serum, human serum, etc.) and is generally designated by the letters SFM. Exemplary though non-limiting serum-free media familiar to the skilled artisan include HuMEC Basal Serum free Medium, KNOCKOUT™ CTS™ XenoFREE ESC/iPSC Medium, STEMPRO™-34 SFM Medium, STEMPRO™ NSC Medium, ESSENTIAL™-8 Medium, Medium 254, Medium, 106, Medium, 131, Medium, 154, Medium, 171, Medium 171, Medium 200, Medium 231, HeptoZYME-SFM, Human Endothelial-SFM, GIBCO® FREESTYLE™ 293 Expression Medium, Medium 154CF/PRF, Medium 154C, Medium 154 CF, Medium 106, Medium 200PRF, Medium 131, Essential™-6 Medium, STEMPRO™-34 Medium, Gibco® Astrocyte Medium, AIM V® Medium CTS™, AMINOMAX™ C-100 Basal Medium, AMINOMAX™-II Complete Medium, CD FORTICHO™ Medium, CD CHO AGT Medium, CHO-S-SFM Medium, GIBCO®FREESTYLE™ CHO Expression Medium, CD OPTICHO™ Medium, CD CHO Medium, CD DG44 Medium, SF-900™ Medium, EXPI293™ Expression Medium, LHC Basal Medium, LHC-8 Medium, 293 SFM Medium, CD 293 Medium, AEM Growth Medium, PER. C6® Cell Medium, AIM V® Medium, EXPILIFE® Medium, Keratinocyte-SFM Medium, LHC Medium, LHC-8 Medium, LHC-9 Medium, and any derivatives or modifications thereof.

The phrase "protein-free" culture media refers to culture media that contain no protein (e.g., no serum proteins such as serum albumin or attachment factors, nutritive proteins such as growth factors, or metal ion carrier proteins such as transferrin, ceruloplasmin, etc.). Preferably, if peptides are present, the peptides are smaller peptides, e.g., di- or tri-peptides. Preferably, peptides of deca-peptide length or greater are less than about 1%, more preferably less than about 0.1%, and even more preferably less than about 0.01% of the amino acids present in the protein free medium.

The phrase "low-protein" culture media as used herein refers to media that contain only low amounts of protein (typically less than about 10%, less than about 5%, less than about 1%, less than about 0.5%, or less than about 0.1%, of the amount or concentration of total protein found in culture media containing standard amounts of protein, such as standard basal medium supplemented with 5-10% serum).

The term "animal derived" material as used herein refers to material that is derived in whole or in part from an animal source, including recombinant animal DNA or recombinant animal protein DNA. Preferred media contain no animal desired material.

The term "expression enhancer" generally refers to one or more liquid (preferably aqueous) additives used to supplement a culture medium formulation in accordance with the presently described embodiments, said additives being selected to improve the yield of expressed protein produced in a transient protein expression system in accordance with the presently described embodiments. The term encompasses any one or more of several compounds that affect cell cycle progression, inhibit apoptosis, slow cell growth and/or promote protein production. In the context of the present invention, the term "expression enhancers" generally refers to any one or more compounds added to a transient transfection system, the presence of which enhances or promotes expression of a target protein by a factor of at least 2 fold up to about 10-fold above the expression level seen in the absence of such expression enhancer(s). Exemplary expression enhancers suitable for use with the presently described embodiments include, though are not limited to, additives such as valproic acid (VPA, acid and sodium salt), sodium propionate, lithium acetate, dimethyl sulfoxide (DMASO), sugars including galactose, amino acid mixtures, or butyric acid, or any combinations of the aforementioned. The optimal concentration of each specific expression enhancer may vary according to individual characteristics of the expression system and the requirements of the user, and the determination of what constitutes an optimal concentration of any one or more expression enhancer in a given experimental scenario is well within purview of a practitioner having ordinary skill level in the art. By way of example only, in some embodiments, the optimal final concentrations ranges of valproic acid (VPA) used in the practice of the present invention may be in the range of about 0.20 mM to about 25 mM. More preferably, the final concentration of VPA may be in the range of about 0.25 mM to about 24 mM, about 0.26 mM to about 23 mM, 0.27 mM to about 23 mM, 0.28 mM to about 23 mM, 0.29 mM to about 22 mM, about 0.30 mM to about 21 mM, about 0.31 mM to about 20 mM, about 0.32 mM to about 19 mM, about 0.33 mM to about 17 mM, about 0.34 mM to about 18 mM, about 0.35 mM to about 17 mM, about 0.36 mM to about 16 mM, about 0.37 mM to about 15 mM, about 0.40 mM to about 14 mM, about 0.41 mM to about 13 mM, about 0.42 mM to about 12 mM, about 0.43 mM to about 11 mM, about 0.44 mM to about 10 mM, about 0.45 mM to about 9 mM, about 0.46 mM to about 8 mM, about 0.47 mM to about 7 mM, about 0.48 mM to about 6 mM, about 0.49 mM to about 5 mM, about 0.50 mM to about 4 mM, about 0.50 mM to about 4 mM, about 0.55 mM to about 3 mM, 0.6 mM to about 2 mM or 0.75 to about 1.5 mM. In some preferred though non-limiting embodiments, the final concentration of VPA used in the practice of the present invention may be between about 0.15 mM to about 1.5 mM, about 0.16 mM to about 1.5 mM, about 0.17 mM to about 1.5 mM, about 0.18 mM to about 1.5 mM, about 0.19 mM to about 1.5 mM, about 0.20 mM to about 1.5 mM, about 0.25 mM to about 1.5 mM, about 0.30 mM to about 1.5 mM, about 0.40 mM to about 1.5 mM, about 0.50 mM to about 1.5 mM, about 0.60 mM to about 1.5 mM, about 0.70 mM to about 1.5 mM, about 0.80 mM to about 1.5 mM, about 0.90 mM to about 1.5 mM or about 0.10 mM to about 1.5 mM. In some preferred though non-limiting embodiments, the final concentration of VPA used in the practice of the present invention may be between about 0.20 to about 1.5 mM, about 0.21 to about 1.4 mM, about 0.22 to about 1.4 mM, about 0.23 to about 1.4 mM, about 0.24 to about 1.4 mM, about 0.25 to about 1.3 mM, about 0.25 to about 1.2 mM, about 0.25 to about 1.1 mM, or about 0.25 to about 1.0 mM.

In further embodiments, the optimal final concentration of sodium propionate (NaPP) used in the practice of the present invention may be in the range of about 0.2 mM to about 100 mM. In certain preferred though non-limiting embodiments, the optimal final concentration of NAPP may be in the range of about 0.5 to about 80 mM, about 0.4 mM to about 70 mM, about 0.5 mM to about 60 mM, about 0.6 mM to about 50 mM, about 0.7 mM to about 40 mM, about 0.8 mM to about 30 mM, about 0.9 mM to about 20 mM, about 1 mM to about 15 mM, about 2 mM to about 10 mM, about 3 mM to about 9 mM, about 4 mM to about 8 mM, or about 5 mM to about 7 mM. In certain preferred though non-limiting embodiments, the optimal final concentration of NAPP may be in the range of about 1 mM to about 10 mM, about 1 mM to about 2 mM, about 2 mM to about 3 mM, about 3 mM to about 4 mM, about 4 mM to about 5 mM, about 5 mM to about 6 mM, about 6 mM to about 7 mM, about 7 mM to about 8 mM, about 8 mM to about 9 mM, or about 9 mM to about 10 mM. In certain preferred though non-limiting embodiments, the optimal final concentration of NAPP may be about 1 mM, about 1.5 mM, about 2 mM, about 2.5 mM, about 3 mM, about 3.5 mM, about 4 mM, about 4.5 mM, about 5 mM, about 5.5 mM, about 6 mM, about 6.5 mM, about 7 mM, about 7.5 mM, about 8 mM, about 8.5 mM, about 9 mM, about 9.5 mM, or about 10 mM.

In further embodiments, the optimal final concentration of lithium acetate (LiAc) used in the practice of the present invention may be in the range of about 0.25 to about 25 mM, about 0.26 mM to about 20 mM, about 0.27 mM to about 15 mM, about 0.28 mM to about 10 mM, about 0.29 mM to about 5 mM, about 0.3 mM to about 4.5 mM, about 0.31 mM to about 4 mM, about 0.35 mM to about 3 mM, about 0.5 mM to about 2.5 mM, about 1 mM to about 3 mM, about 1.5 mM to about 2.5 mM, or about 2 mM to about 3 mM.

In further embodiments, the optimal final concentration of butyric acid used in the practice of the present invention may be in the range of about 0.25 to about 25 mM, about 0.26 mM to about 20 mM, about 0.27 mM to about 15 mM, about 0.28 mM to about 10 mM, about 0.29 mM to about 5 mM, about 0.3 mM to about 4.5 mM, about 0.31 mM to about 4 mM, about 0.35 mM to about 3 mM, about 0.5 mM to about 2.5 mM, about 1 mM to about 3 mM, about 1.5 mM to about 2.5 mM, or about 2 mM to about 3 mM.

An expression enhancer used in accordance with the present invention may be added to the culture medium immediately prior to transfection or after transfection prior to harvesting the cells and the expressed protein. In some specific though non-limiting embodiments described below, "Enhancer 1" generally refers to 0.25 mM-1 mM valproic acid, and "Enhancer 2" generally refers to 5 mM-7 mM sodium propionate. However, if indicated otherwise, the terms Enhancer 1 and Enhancer 2 may encompass different enhancer compounds. Expression enhancers may be added to a culture medium sequentially, or as a cocktail.

The term "vector," as used herein, is intended to refer to a nucleic acid molecule capable of transporting another nucleic acid to which it has been linked. One type of vector is a "plasmid," which refers to a circular double stranded DNA into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors," or simply, "expression vectors." In general, expression vectors of utility in recombinant DNA techniques are often in the form of plasmids. In the present specification, "plasmid" and "vector" may be used interchangeably as the plasmid is the most commonly used form of vector. Certain vectors used in accordance with the practice of invention described herein may be well-known vectors used in the art, such as, e.g., pCDNA 3.3, or a modified version thereof. Non-limiting examples of the types of modification to a vector that may be suitable in the practice of the present invention include, though are not limited to, modification such as the addition of modification of one or more enhancers, one or more promoters, one or more ribosomal binding sites, one or more origins of replication, or the like. In certain preferred though non-limiting embodiments, and expression vector used in the practice of the present invention may include one or more enhancer elements selected to improve expression of the protein of interest in the present transient expression system. The selected enhancer element may be positioned 5' or 3' to the expressible nucleic acid sequence used to express the protein of interest. A particularly preferred though non-limiting enhancer element is the woodchuck hepatitis post-transcriptional regulatory element (WPRE).

As used herein, the phrase "expression vector containing a genetic sequence capable of producing an expressed protein" generally refers to a vector as defined above which is capable to accommodating an expressible nucleic acid sequence having at least one open-reading frame of a desired protein of interest (said protein of interest being selected by the user of the present invention) in additional to one or more nucleic acid sequences or elements that are required to support the expression thereof in a cell or in a cell-free expression system. Such additional nucleic acid sequences or elements that may be present in an expression vector as defined herein may include, one or more promoter sequences, one or more enhancer elements, one or more ribosomal binding sites, one or more translational initiation sequences, one or more origins of replication, or one or more selectable markers. A variety of nucleic acid sequences or elements serving this purpose are familiar to the skilled artisan, and the selection of one or more thereof for use in the practice of the present invention is well within the purview of the skilled practitioner.

The terms "polynucleotide" and "nucleic acid" as used herein refers to any nucleic acid, including deoxyribonucleic acid (DNA) and ribonucleic acid (RNA). In preferred embodiments, "nucleic acid" refers to DNA, including genomic DNA, complementary DNA (cDNA), and oligonucleotides, including oligo DNA. In certain preferred though non-limiting embodiments, "nucleic acid' refers to genomic DNA and/or cDNA. The nucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may comprise modification(s) made after synthesis, such as conjugation to a label. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotides(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl-, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs, and basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR$_2$ ("amidate"), P(O)R, P(O)OR', CO, or CH2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, generally refers to short, generally single-stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

As used herein, the phrase "first period of time", when used in the context of a method for transiently transfecting cells in accordance with the methods of the invention described herein generally refers to the time interval between transfecting a population of cells with an expressible nucleic acid and the additional of one or more expression enhancers to the transfected cells. Typically, a first period of time will be in the range of about 2 hrs to about 4 days. In certain preferred though non-limiting embodiments, a first period of time may be in the range of about 3 to about 90 hrs, about 4 to about 85 hr, about 5 to about 80 hrs, about 6 to about 75 hrs, about 7 to about 70 hrs, about 8 to about 65 hrs, about 9 to about 60 hrs, about 10 to about 55 hrs, about 11 to about 50 hrs, about 12 to about 45 hrs, about 13 to about 40 hrs, about 14 to about 35 hrs, about 15 to 30 hrs, about 16 to about 24 hrs, about 17 to about 24 hrs, about 18 to about 24 hrs, about 19 to about 24 hrs, about 20 to about 24 hrs, about 21 to about 24 hrs, about 22 to about 24 hrs or about 23 to about 24 hrs. In other preferred to non-limiting embodiments, a first period of time may be up to about 15 hrs, up to about 16 hrs, up to about 17 hrs, up to about 18 hrs, up to about 19 hrs, up to about 20 hrs, up to about 21 hrs, up to about 22 hrs, up to about 23 hrs, up to about 24 hrs, up to about 25 hrs, up to about 26 hrs, up to about 27 hrs, up to about 28 hrs, up to about 29 hrs or up to about 30 hrs.

As used herein, the phrase "second period of time", when used in the context of a method for transiently transfecting cells in accordance with the methods of the invention described herein generally refers to the time interval between the addition of one or more expression enhancers and either the addition of one or more additional enhancers, or the harvesting of the transfected cells and purification or isolation of the protein expressed therein. Typically, a second period of time will be in the range of about 10 hrs to about 10 days, though other time intervals may be used if determined to be optimal for the protein being expressed. In some preferred though non-limiting embodiments, the second period of time may be in the range of 2 hrs to 5 days, 2.5 hrs to 4 days, about 3 to about 90 hrs, about 4 to about 85 hr, about 5 to about 80 hrs, about 6 to about 75 hrs, about 7 to about 70 hrs, about 8 to about 65 hrs, about 9 to about 60 hrs, about 10 to about 55 hrs, about 11 to about 50 hrs, about 12 to about 45 hrs, about 13 to about 40 hrs, about 14 to about 35 hrs, about 15 to 30 hrs, about 16 to about 24 hrs, about 17 to about 24 hrs, about 18 to about 24 hrs, about 19 to about 24 hrs, about 20 to about 24 hrs, about 21 to about 24 hrs, about 22 to about 24 hrs or about 23 to about 24 hrs. In other preferred to non-limiting embodiments, a first period of time may be up to about 15 hrs, up to about 16 hrs, up to about 17 hrs, up to about 18 hrs, up to about 19 hrs, up to about 20 hrs, up to about 21 hrs, up to about 22 hrs, up to about 23 hrs, up to about 24 hrs, up to about 25 hrs, up to about 26 hrs, up to about 27 hrs, up to about 28 hrs, up to about 29 hrs or up to about 30 hrs.

As used herein the phrase "third period of time", when used in the context of a method for transiently transfecting cells in accordance with the methods of the invention described herein generally refers to the time interval between the addition of at least a first expression enhancer and at least a second expression enhancer. The time interval between the addition of a first and second expression enhancer may be on the order of seconds to days, though in some embodiments such first and second expression enhancer may be added essentially simultaneous, or may optionally be provided in a single formulation.

As used herein the terms "complexation reaction," "complexation media" or the like, generally refer to a physiologically acceptable culture media or reaction in which a nucleic acid is complexed to a transfection reagent formulation. Typically, a nucleic acid that is to be introduced into a cell for the purpose of expressing a protein is first complexed with a suitable transfection reagent (such as, e.g., a cationic lipid formulation) to lipid/nucleic acid complexes or aggregates.

By "transition element" or "transition metal" (which can be used interchangeably) is meant an element in which an inner electron valence shell, rather than an outer shell, is only partially filled, such that the element acts as a transitional link between the most and least electropositive in a given series of elements. Transition elements are typically characterized by high melting points, high densities, high dipole or magnetic moments, multiple valencies, and the ability to form stable complex ions. Examples of such transition elements useful in the present invention include scandium (Sc), titanium (Ti), vanadium (V), chromium (Cr), manganese (Mn), iron (Fe), cobalt (Co), nickel (Ni), copper (Cu), zinc (Zn), yttrium (Y), zirconium (Zr), niobium (Nb), molybdenum (Mo), technetium (Tc), rubidium (Ru), rhodium (Rh), palladium (Pd), silver (Ag), cadmium (Cd), lanthanum (La), hafnium (Hf), tantalum (Ta), tungsten (W), rhenium (Re), osmium (Os), iridium (Ir), platinum (Pt), gold (Au), mercury (Hg), and actinium (Ac). Of particular interest as a transition element for use in culture media compositions, including those of the present invention, are ions, chelates, salts, and complexes of iron ($Fe^{2+}$ or $Fe^{3+}$).

A variety of techniques and reagents are available for the introduction of macromolecules into a target cell in a process known as "transfection". Commonly used reagents include, for example, calcium phosphate, DEAE-dextran and lipids. For examples of detailed protocols for the use of reagents of these types, numerous references texts are available for example, Current Protocols in Molecular Biology, Chapter 9, Ausubel, et al. Eds., John Wiley and Sons, 1998. Additional methods for transfecting cells are known in the art, and may include electroporation (gene electrotransfer), sono-poration, optical transfection, protoplast fusion, impalefection, magnetofection, or viral transduction.

A "reagent for the introduction of macromolecules" into cells or a "transfection reagent" is any material, formulation or composition known to those of skill in the art that facilitates the entry of a macromolecule into a cell. For example, see U.S. Pat. No. 5,279,833. In some embodiments, the reagent can be a "transfection reagent" and can be any compound and/or composition that increases the uptake of one or more nucleic acids into one or more target cells. A variety of transfection reagents are known to those skilled in the art. Suitable transfection reagents can include, but are not limited to, one or more compounds and/or compositions comprising cationic polymers such as polyethyleneimine (PEI), polymers of positively charged amino acids such as polylysine and polyarginine, positively charged dendrimers and fractured dendrimers, cationic β-cyclodextrin containing polymers (CD-polymers), DEAE-dextran and the like. In some embodiments, a reagent for the introduction of macromolecules into cells can comprise one or more lipids which can be cationic lipids and/or neutral lipids. Preferred lipids include, but are not limited to, N-[1-(2,3-dioleyloxy) propyl]-N,N,N-trimethylamonium chloride (DOTMA), dioleoylphosphatidylcholine (DOPE), 1,2-Bis(oleoyloxy)-3-(4'-trimethylammonio) propane (DOTAP), 1,2-dioleoyl-3-(4'-trimethylammonio) butanoyl-sn-glycerol (DOTB), 1,2-dioleoyl-3-succinyl-sn-glycerol choline ester (DOSC), cholesteryl (4'-trimethylammonio)butanoate (ChoTB), cetyltrimethylammonium bromide (CTAB), 1,2-dioleoyl-3-dimethyl-hydroxyethyl ammonium bromide (DORI), 1,2-dioleyloxypropyl-3-dimethyl-hydroxyethyl ammonium bromide (DORIE), 1,2-dimyristyloxypropyl-3-dimethyl-hydroxyethyl ammonium bromide (DMRIE), O,O'-didodecyl-N-[p(2-trimethylammonioethyloxy)benzoyl]-N,N,N-trimethylam-monium chloride, spermine conjugated to one or more lipids (for example, 5-carboxyspermylglycine dioctadecylamide (DOGS), $N,N^I,N^{II},N^{III}$-tetramethyl-$N,N^I$, $N^{II},N^{III}$-tet-rapalmitylspermine (TM-TPS) and dipalmitoyl-phasphatidylethanolamine 5-carboxyspermylaminde (DPPES)), lipopolylysine (polylysine conjugated to DOPE), TRIS (Tris(hydroxymethyl)aminomethane, tromethamine) conjugated fatty acids (TFAs) and/or peptides such as trily-syl-alanyl-TRIS mono-, di-, and tri-palmitate, (3β-[N—(N',N'-dimethylaminoethane)-carbamoyl] cholesterol (DC-Chol), N-(α-trimethylammonioacetyl)-didodecyl-D-glutamate chloride (TMAG), dimethyl dioctadecylammonium bromide (DDAB), 2,3-dioleyloxy-N-[2(spermine-carboxamido)ethyl]-N,N-dimethyl-1-pro-panamin-iniumtrifluoroacetate (DOSPA) and combinations thereof.

Those skilled in the art will appreciate that certain combinations of the above mentioned lipids have been shown to be particularly suited for the introduction of nucleic acids into cells for example a 3:1 (w/w) combination of DOSPA and DOPE is available from Life Technologies Corporation, Carlsbad, Calif. under the trade name LIPO-FECTAMINE™, a 1:1 (w/w) combination of DOTMA and DOPE is available from Life Technologies Corporation, Carlsbad, Calif. under the trade name LIPOFECTIN®, a 1:1 (M/M) combination of DMRIE and cholesterol is available from Life Technologies Corporation, Carlsbad, Calif. under the trade name DMRIE-C reagent, a 1:1.5 (M/M) combination of TM-TPS and DOPE is available from Life Technologies Corporation, Carlsbad, Calif. under the trade name CellFECTIN® and a 1:2.5 (w/w) combination of DDAB and DOPE is available from Life Technologies Corporation, Carlsbad, Calif. under the trade name LipfectACE®. In addition to the above-mentioned lipid combinations, other formulations comprising lipids in admixture with other compounds, in particular, in admixture with peptides and proteins comprising nuclear localization sequences, are known to those skilled in the art. For example, see international application no. PCT/US99/26825, published as WO 00/27795, both of which are incorporated by reference herein.

Lipid aggregates such as liposomes have been found to be useful as agents for the delivery of macromolecules into cells. In particular, lipid aggregates comprising one or more cationic lipids have been demonstrated to be extremely efficient at the delivery of anionic macromolecules (for example, nucleic acids) into cells. One commonly used cationic lipid is N-[1-(2,3-dioleoyloxy)propyl]-N,N,N-trimethylammonium chloride (DOTMA). Liposomes comprising DOTMA alone or as a 1:1 mixture with dioleoylphosphatidylethanolamine (DOPE) have been used to introduce nucleic acids into cells. A 1:1 mixture of DOTMA:DOPE is commercially available from Life Technologies Corporation, Carlsbad, Calif. under the trade name of LIPOFECTIN™. Another cationic lipid that has been used to introduce nucleic acids into cells is 1,2-bis(oleoyl-oxy)-3-3-(trimethylammonia) propane (DOTAP). DOTAP differs from DOTMA in that the oleoyl moieties are linked to the propylamine backbone via ether bonds in DOTAP whereas they are linked via ester bonds in DOTMA. DOTAP is believed to be more readily degraded by the target cells. A structurally related group of compounds wherein one of the methyl groups of the trimethylammonium moiety is replaced with a hydroxyethyl group are similar in structure to the Rosenthal inhibitor (RI) of phospholipase A (see Rosenthal, et al., (1960) J. Biol. Chem. 233:2202-2206.). The RI has stearoyl esters linked to the propylamine core. The dioleoyl analogs of RI are commonly abbreviated DOR1-ether and DOR1-ester, depending upon the linkage of the lipid moiety to the propylamine core. The hydroxyl group of the hydroxyethyl moiety can be further derivatized, for example, by esterification to carboxyspermine.

Another class of compounds which has been used for the introduction of macromolecules into cells comprise a carboxyspermine moiety attached to a lipid (see, Behr, et al., (1989) Proceedings of the National Academy of Sciences, USA 86:6982-6986 and EPO 0 394 111). Examples of compounds of this type include dipalmitoylphosphatidylethanolamine 5-carboxyspermylamide (DPPES) and 5-carboxyspermylglycine dioctadecylamide (DOGS). DOGS is commercially available from Promega, Madison, Wis. under the trade name of TRANSFECTAM™.

A cationic derivative of cholesterol (3β-[N—(N',N'-dimethylaminoethane)-carbamoyl]cholesterol, DC-Chol) has been synthesized and formulated into liposomes with DOPE (see Gao, et al., (1991) BBRC 179(1):280-285.) and used to introduce DNA into cells. The liposomes thus formulated were reported to efficiently introduce DNA into the cells with a low level of cellular toxicity. Lipopolylysine, formed by conjugating polylysine to DOPE (see Zhou, et al., (1991) BBA 1065:8-14), has been reported to be effective at introducing nucleic acids into cells in the presence of serum.

Other types of cationic lipids that have been used to introduce nucleic acids into cells include highly packed polycationic ammonium, sulfonium and phosphonium lipids such as those described in U.S. Pat. Nos. 5,674,908 and 5,834,439, and international application no. PCT/US99/26825, published as WO 00/27795. One particularly preferred though non-limiting transfection reagent for delivery of macromolecules in accordance with the present invention is LIPOFECTAMINE 2000™ which is available from Life technologies (see U.S. international application no. PCT/US99/26825, published as WO 00/27795). Another preferred though non-limiting transfection reagent suitable for delivery of macromolecules to a cell is EXPI-FECTAMINE™. Other suitable transfection reagents include LIOFECTAMINE™ RNAiMAX, LIPOFECTAMINE™ LTX, OLIGOFECTAMINE™, Cellfectin™, INVIVOFECTAMINE™, INVIVOFECTAMINE™ 2.0, and any of the lipid reagents or formulations disclosed in U.S. Patent Appl. Pub. No. 2012/0136073, by Yang et al. (incorporated herein by reference thereto). A variety of other transfection reagents are known to the skilled artisan and may be evaluated for the suitability thereof to the transient transfection systems and methods described herein.

The present invention is directed to a high-yield transient transfection system that supports (a) the introduction of at least one macromolecule, preferably an expressible nucleic acid molecule, into eukaryotic cells in culture, (b) the cultivation of cells into which at least one macromolecule is introduced, and optionally (c) the production of recombinant protein product or expression of the nucleic acid in cells into which at least one macromolecule is introduced, wherein medium containing the macromolecule does not need to be removed from the culture and replaced with fresh medium after introduction of at least one macromolecule into cells and prior to cultivation and production of protein product or expression of nucleic acid.

The transient transfection system of the present invention, an the use thereof in accordance with the methods described herein, results in the rapid and reproducible expression of high levels of a protein of interest in a cell culture system. Typically, the present transient transfection systems and methods are capable of producing recombinant expressed protein at levels in the range of about 200 µg protein/L of culture to about 2 g protein/L of culture, depending on the individual expression characteristics of the desired recombinant protein and cell type used. Using the transient transfection system and methods provided for herein, a user may obtain levels of expressed protein that are about 2-fold to up to about 20-fold in excess of what is currently obtainable using standard commercially available transient transfection systems. Using the transient transfection system and methods provided for herein, a user may obtain levels of expressed protein that is about 2.5-fold, about 3-fold, about 3.5-fold, about 4-fold, about 4.5-fold, about 5-fold, about 5.5-fold, about 6-fold, about 6.5-fold, bout 7-fold, about 7.5-fold, about 8-fold, about 8.5-fold, about 9-fold, about 9.5-fold, or up to about 10-fold or greater than that seen with contemporary transient expression systems. For example, using the present transient transfection system to produce a recombinant protein, a user may obtain a protein yield between about 2-fold up to about 10-fold higher than the protein yield obtained using a commercially available transient transfection system optimized for production of recombinant protein in suspension cells, such as, e.g., FREE-STYLE™ Expression System.

Using the system of the present invention, which system includes, among other elements, at least a high density culture medium, at least a population of suspension cells adapted for high density growth, optionally one or more expression vectors, optionally one or more transfection reagents, and optionally one or more expression enhancers, it is not necessary to replenish, replace or supplement the medium after one has introduced at least one macromolecule into at least one cell, and before cells into which at least one macromolecule has been introduced are further cultured to produces protein product or express a nucleic acid. In the system of the present invention, the medium is ideally a serum-free medium and/or a chemically defined medium and/or protein free or substantially low protein medium, and/or a medium that does not contain animal derived components, or a medium having combinations of these features.

In one non-limiting aspect of the invention, with respect to the introduction of compounds or macromolecules (e.g., nucleic acid) into cells in culture, the high yield culture medium of the present invention facilitates higher cell transfection efficiency than can typically be obtained using presently available transient transfection systems. In another related though non-limiting aspect of the invention, the system also does not require transfecting the cells in a smaller volume than cells are to be cultured in after transfection. In yet another related though non-limiting aspect of the present invention, the system facilitates higher cell viability than presently available transient transfection systems. In yet a further related though non-limiting aspect still, the system facilitates higher cell density (i.e., cells/ml of culture medium) than presently available transient transfection systems. In another related though non-limiting aspect of the present invention, the system facilitates a higher level of recombinant protein expression in cells in culture than presently available transient transfection systems. Preferably, though not necessarily, the same volume of medium can be used for to introduce at least one macromolecule into a cell and subsequent cultivation without having to replace, remove, supplement or replenish the medium in which the transfection of the cells has occurred. Alternatively, the cells are divided or medium volume is increased less from about 2, about 5, about 8 or about 10 times.

The medium, methods, kit and composition of the present invention are intended to be used to introduce at least one macromolecule or to transfect and culture cells in any volume of culture medium. Such introduction is preferably accomplished in 0.1 to 10 times the amount of medium used to culture cells to be transfected. Preferably, the cell culture volume is greater than about one milliliter. More preferably, the cell culture volume is from about 200 µl to 100 liters. More preferably, the cell culture volume is from about 2 ml to about 50 liters, most preferably from about 5 ml to about 5 liters. More preferably, the cell culture volume is from about 100 ml to about 50 liters. More preferably, the cell culture volume is from about 500 ml to about 50 liters. More preferably, the cell culture volume is from about 500 ml to about 25 liters. More preferably, the cell culture volume is from about 500 ml to about 10 liters. More preferably, the cell culture volume is from about 500 ml to about 5 liters. More preferably, the cell culture volume is from about 500 ml to about 1 liter.

In the medium, methods, kit and composition of the present invention, the medium optionally does not contain compounds that can interfere with introduction of macromolecules or transfection, e.g., polyanionic compounds such as polysulfonated and/or polysulfated compounds. Preferably, the medium does not contain dextran sulfate.

The medium, methods, kit and composition of the present invention permit the introduction of compounds or macromolecules (particularly macromolecules, for example nucleic acids, proteins and peptides) into the cultured cells (for example by transfection) without the need to change the medium. In one preferred embodiment, the present invention provides a medium for the cultivation and transfection of eukaryotic cells.

Using the medium, methods, kit and composition of the present invention, those of ordinary skill in the art can introduce macromolecules or compounds (e.g., nucleic acid) into cells in culture. Preferably, the macromolecule or compound (e.g., nucleic acid) is introduced into at least about 20 percent of the cells. More preferably, the macromolecule or compound (e.g., nucleic acid) is introduced into about 20 to about 100 percent of the cells. More preferably, the macromolecule or compound (e.g., nucleic acid) is introduced into about 30 to about 100 percent of the cells. More preferably, the macromolecule or compound (e.g., nucleic acid) is introduced into about 50 to about 100 percent of the cells. Practically, the macromolecule or compound might be introduced into about 20% to about 90% of the cells, about 20% to about 80% of the cells, about 30% to about 60, 70, 80 or 90% of the cells, about 20, 30, 40 or 50% to about 70, 75, 80, 85, 90, 95 or 98% of the cells, etc. Even about 60, 70, 75 or 80 to about 90% or close to 100% of the cells may contain the introduced molecule or compound.

In preferred embodiments of the medium, methods, kit and composition of the present invention, one or more undesirable components (i.e., one or more serum components, one or more undefined components, one or more protein components and/or one or more animal derived components) have been substituted or replaced in one or more functions by one or more replacement compounds.

Replacement compounds of the invention may optionally include one or more metal binding compounds and/or one or more transition element complexes, said complexes comprising one or more transition elements or a salts or ions thereof, in a complex with one or more metal-binding compounds. Preferably, the medium is capable of supporting the cultivation of a cell in vitro in the absence of one or more naturally derived metal carriers, such as transferrin, or other animal derived proteins or extracts. The metal binding compound can be in a complex with a transition metal prior to addition of the metal binding compound to the medium. In other embodiments, the metal binding compound is not in a complex with a transition metal prior to addition of the metal binding compound to the media. Preferably, the medium of the present invention does not contain transferrin and/or does not contain insulin.

The present invention also relates to a cell culture medium obtained by combining a medium with one or more replacement compounds. Preferably, the medium can be a serum-free medium and/or a chemically defined medium and/or a protein-free or low protein medium and/or can be a medium lacking animal derived components. The medium preferably does not contain transferrin and/or does not contain insulin. In some preferred embodiments, the medium can be capable of supporting the cultivation of a cell in vitro and/or can permit the introduction of macromolecules into the cell. In some embodiments, one or more of the replacement compounds can be a metal binding compound and/or can be a transition element complex, said complex comprising at least one transition element or a salt or ion thereof complexed to at least one metal-binding compound. Preferred transition elements, metal-binding compounds, and transition element complexes for use in this aspect of the invention include those described in detail herein.

Replacement compounds of the present invention can facilitate the delivery of transition metals to cells cultured in vitro. In preferred embodiments, the replacement compounds can deliver iron and replace transferrin. A preferred replacement compound is a hydroxypyridine derivative. Preferably, the hydroxypyridine derivative is selected from the group consisting of 2-hydroxypyridine-N-oxide, 3-hydroxy-4-pyrone, 3-hydroxypypyrid-2-one, 3-hydroxypyrid-2-one, 3-hydroxypyrid-4-one, 1-hydroxypyrid-2-one, 1,2-dimethyl-3-hydroxypyrid-4-one, 1-methyl-3-hydroxypyrid-2-one, 3-hydroxy-2(1H)-pyridinone, and pyridoxal isonicotinyl hydrazone, nicotinic acid-N-oxide, 2-hydroxynicotinic acid. Most preferably, the hydroxypyridine derivative is 2-hydroxypyridine-N-oxide.

The replacement compounds of the present invention can be used with any media, including media for cultivating or growing eukaryotic and/or prokaryotic cells, tissues, organs, etc. Such media include, but are not limited to, CD FORTICHO™ Medium, Expi293™ Expression Media, Dulbecco's Modified Eagle's Medium (DMEM), Minimal Essential Medium (MEM), Basal Medium Eagle (BME), RPMI-1640, Ham's F-10, Ham's F-12, aMinimal Essential Medium (aMEM), Glasgow's Minimal Essential Medium (G-MEM), and Iscove's Modified Dulbecco's Medium (IMDM). Other media that are commercially available (e.g., from Life Technologies Corporation, Carlsbad, Calif.) or that are otherwise known in the art can be equivalently used in accordance with the present invention including, but not limited to, 293 SFM, CD-CHO medium, VP SFM, BGJb medium, Brinster's BMOC-3 medium, cell culture freezing medium, CMRL media, EHAA medium, eRDF medium, Fischer's medium, Gamborg's B-5 medium, GLUTAMAX™ supplemented media, Grace's insect cell media, HEPES buffered media, Richter's modified MEM, IPL-41 insect cell medium, Leibovitz's L-15 media, McCoy's 5A media, MCDB 131 medium, Media 199, Modified Eagle's Medium (MEM), Medium NCTC-109, Schneider's Drosophila medium, TC-100 insect medium, Waymouth's MB 752/1 media, William's Media E, protein free hybridoma medium II (PFHM II), AIM V media, Keratinocyte SFM, defined Keratinocyte SFM, STEMPRO® SFM, STEMPRO® complete methylcellulose medium, HepatoZYME-SFM, Neurobasal™ medium, Neurobasal-A medium, Hibernate™ A medium, Hibernate E medium, Endothelial SFM, Human Endothelial SFM, Hybridoma SFM, PFHM II, Sf 900 medium, Sf 900 II SFM, EXPRESS FIVE® medium, CHO-S-SFM, AMINOMAX-II complete medium, AMINOMAX-C100 complete medium, AMINOMAX-C 100 basal medium, PB-MAX™ karyotyping medium, KARYOMAX bone marrow karyotyping medium, KNOCKOUT D-MEM and $CO_2$ independent medium. The above media are obtained from manufacturers known to those of ordinary skill in the art, such as JRH, Sigma, HyClone, and BioWhittaker. Additional examples of media suitable for use in the practice of the present invention can be found in U.S. Pat. Nos. 5,135,866 and 5,232,848 as well as in international publications nos. WO 88/02774, WO 98/15614, WO 98/08934 and European Patent No. 0 282 942, the entireties of which are specifically incorporated herein by reference.

The present invention also provides a method for introducing macromolecules into cells, comprising culturing cells in a medium of the invention and contacting the cells in the medium with one or more macromolecules under conditions causing the macromolecules to be taken up by one or more of the cells. Preferably, the medium is a serum-free medium and/or a chemically defined medium and/or a protein-free or low protein medium and/or can be a medium lacking animal derived components. Preferred cells include eukaryotic cells. More preferably, the cells are mammalian cells. The medium can comprise one or more replacement compounds and preferably does not contain transferrin and/or does not contain insulin. In some preferred embodiments, the medium permits the growth and transfection of the cell in the same medium. In some embodiments, the macromolecules can comprise one or more nucleic acids and conditions causing the nucleic acid molecules to be taken up by the cells include contacting the nucleic acid with a reagent which causes the nucleic acid to be introduced into one or more cells.

The present invention also provides a composition comprising a medium of the invention and a cell. Preferably, the medium is a serum-free medium and/or a chemically defined medium and/or a protein-free or low protein medium and/or a medium lacking animal derived components. Preferred cells include eukaryotic cells. More preferably, the cells are mammalian cells. Most preferred are suspension cells derived from 293 fibroblasts. The medium can comprise one or more replacement compounds and preferably does not contain transferrin and/or does not contain insulin. Preferably, the medium supports the growth and transfection of the cell in the same medium, more preferably, the medium supports the growth and cultivation of mammalian cells expressing a recombinant protein, where said medium does not have to be replenished, replaced or otherwise supplemented after the introduction of an expressible nucleic acid therein for the purposes of producing a recombinant protein.

The present invention also provides compositions comprising a medium of the present invention and one or more reagents for the introduction of macromolecules into one or more cells. Preferably, the medium is a serum-free medium and/or a chemically defined medium and/or a protein-free or low protein medium and/or a medium lacking animal derived components. The medium can comprise one or more replacement compounds and preferably does not contain transferrin and/or does not contain insulin. Preferably, the medium contains a transfection reagent and the macromolecules are nucleic acids. The macromolecules might also be proteins and/or peptides. In some embodiments, the reagent comprises one or more lipids of which one or more can be cationic lipids. More preferably, the reagent comprises a mixture of neutral and cationic lipids. In some embodiments, the reagent comprises one or more peptides and/or proteins which can be provided alone or in admixture with one or more lipids.

The present invention also provides compositions comprising a medium of the invention and one or more macromolecules to be introduced into a cell. Preferably, the medium is a serum-free medium and/or a chemically defined medium and/or a protein-free or low protein medium and/or a medium lacking animal derived components. The medium can comprise one or more replacement compounds and preferably does not contain transferrin and/or does not contain insulin. The macromolecules can be, for example, nucleic acids and/or proteins and/or peptides and can be uncomplexed or can be in the form of a complex with one or more reagents for the introduction of macromolecules into cells. Preferably, the macromolecules are nucleic acids and can be in the form of a complex with one or more transfection reagents.

The present invention also provides a composition comprising at least one component (or combination thereof) selected from the group consisting of a medium of the present invention, at least one cell, at least one macromolecule, at least one reagent for introducing at least one macromolecule into at least one cell. Preferably, the cells are eukaryotic cells. More preferably, the cells are mammalian cells. Preferably, the medium is a serum-free medium and/or a chemically defined medium and/or a protein-free or low protein medium and/or a medium lacking animal derived components. The medium can comprise one or more replacement compounds and preferably does not contain transferrin and/or does not contain insulin. In some preferred embodiments, the reagent is a transfection reagent and the macromolecules are nucleic acids, for example RNA and/or DNA. Alternatively, the macromolecules are proteins and/or peptides.

In some embodiments, the reagent comprises one or more lipids of which one or more can be cationic lipids. More preferably, the reagent comprises a mixture of neutral and cationic lipids. In some embodiments, the reagent comprises one or more peptides and/or proteins which can be provided alone or in admixture with one or more lipids. In preferred embodiments, the reagent complexes with the macromolecule to introduce the macromolecule into the cell.

The present invention also provides kits for the culture and transfection of cells comprising at least one container comprising a medium for the culture and transfection of cells. Such kits may also comprise at least one component (or a combination thereof) selected from the group consisting of a medium of the present invention, at least one cell, at least one macromolecule, at least one reagent for introducing at least one macromolecule into at least one cell, at least one buffer or buffering salt, and instructions for using the kit to introduce at least one macromolecule into at least one cell. Preferably, the medium is a serum-free medium and/or a chemically defined medium and/or a protein-free or low protein medium and/or a medium lacking animal derived components. The medium can comprise one or more replacement compounds and preferably does not contain transferrin and/or does not contain insulin and/or does not contain an animal growth factor. The medium can comprise one or more replacement compounds that can be metal binding compounds and/or can comprise one or more complexes comprising one or more replacement compounds. In some embodiments, the medium can comprise one or more complexes, said complex comprising one or more transition elements or salts or ions thereof complexed one or more replacement compounds which can be metal-binding compounds. In some embodiments, said medium is capable of supporting the cultivation of a cell in vitro and permits transfection of cells cultured therein. In some embodiments, kits of the invention can further comprise at least one container comprising a lipid for transfecting cells. In some embodiments, the kits of the invention can comprise at least one container comprising a nucleic acid.

According to one aspect of the invention, a transition element is preferably selected from the group consisting of scandium, titanium, vanadium, chromium, manganese, iron, cobalt, nickel, copper, zinc, yttrium, zirconium, niobium, molybdenum, technetium, rubidium, rhodium, palladium, silver, cadmium, lanthanum, hafnium, tantalum, tungsten, rhenium, osmium, iridium, platinum, gold, mercury, and actinium, or salts or ions thereof, and is preferably an iron salt. Suitable iron salts include, but are not limited to, $FeCl_3$, $Fe(NO_3)_3$ or $FeSO_4$ or other compounds that contain $Fe^{+++}$ or $Fe^{++}$ ions.

Preferred replacement compounds include, but are not limited to, metal-binding compounds. See, for example, international patent application no. PCT/US00/23580, Publication No. WO 01/16294.

Metal binding compounds of the present invention include any macromolecules which can interact with or bind with transition elements and facilitate their uptake by cells. Such interaction/binding can be covalent or non-covalent in nature. The metal-binding compound used in this aspect of the invention is preferably selected from the group consisting of a polyol, a hydroxypyridine derivative, 1,3,5-N,N',N"-tris(2,3-dihydroxybenzoyl)amino-methylbenzene, ethylenediamine-N,N'-tetramethylenephosphonic acid, trisuccin, an acidic saccharide (e.g., ferrous gluconate), a glycosaminoglycan, diethylenetriaminepentaacetic acid, nicotinic acid-N-oxide, 2-hydroxy-nicotinic acid, mono-, bis-, or tris-substituted 2,2'-bipyridine, a hydroxamate derivative (e.g. acetohydroxamic acid), an amino acid derivative, deferoxamine, ferrioxamine, iron basic porphine and derivatives thereof, DOTA-lysine, a texaphyrin, a sapphyrin, a polyaminocarboxylic acid, an α-hydroxycarboxylic acid, a polyethylenecarbamate, ethyl maltol, 3-hydroxy-2-pyridine, and IRCO11. In one preferred embodiment, the metal-binding compound is a polyol such as sorbitol or dextran, and particularly sorbitol. In a related embodiment, the metal-binding compound is a hydroxypyridine derivative, such as 2-hydroxypyridine-N-oxide, 3-hydroxy-4-pyrone, 3-hydroxypyrid-2-one, 3-hydroxypyrid-2-one, 3-hydroxypyrid-4-one, 1-hydroxypyrid-2-one, 1,2-dimethyl-3-hydroxypyrid-4-one, 1-methyl-3-hydroxypyrid-2-one, 3-hydroxy-2(1H)-pyridinone, ethyl maltol or pyridoxal isonicotinyl hydrazone, and is preferably 2-hydroxypyridine-N-oxide. In particularly preferred embodiments according to this aspect of the invention, the transition metal complex can be a sorbitol-iron complex or 2-hydroxypyridine-N-oxide-iron complex. The metal binding compounds of the present invention can also bind divalent cations such as $Ca^{++}$ and $Mg^{++}$.

The invention relates to cell culture media comprising one or more replacement compounds which can be metal-binding compounds and further comprising one or more ingredients selected from the group of ingredients consisting of at least one amino acid (such as L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine or L-valine, N-acetyl-cysteine), at least one vitamin (such as biotin, choline chloride, D-Ca$^{++}$-pantothenate, folic acid, i-inositol, niacinamide, pyridoxine, riboflavin, thiamine or vitamin B12), at least one inorganic salt (such as a calcium salt, $CuSO_4$, $FeSO_4$, $Fe(NO_3)_3$, $FeCl_3$, KCl, a magnesium salt, a manganese salt, sodium acetate, NaCl, $NaHCO_3$, $Na_2HPO_4$, $Na_2SO_4$, a selenium salt, a silicon salt, a molybdenum salt, a vanadium salt, a nickel salt, a tin salt, $ZnCl_2$, $ZnSO_4$ or other zinc salts), adenine, ethanolamine, D-glucose, one or more cytokines, heparin, hydrocortisone, lipoic acid, phenol red, phosphoethanolamine, putrescine, sodium pyruvate, triiodothyronine, PLURONIC F68, and thymidine.

The culture media of the present invention can optionally include one or more buffering agents. Suitable buffering agents include, but are not limited to, N-[2-hydroxyethyl]-piperazine-N'-[2-ethanesulfonic acid] (HEPES), MOPS, MES, phosphate, bicarbonate and other buffering agents suitable for use in cell culture applications. A suitable buffering agent is one that provides buffering capacity without substantial cytotoxicity to the cells cultured. The selection of suitable buffering agents is within the ambit of ordinary skill in the art of cell culture.

According to the invention, a medium suitable for use in forming the cell culture media of the invention can comprise one or more ingredients, and can be obtained, for example, by combining one or more ingredients selected from the group consisting of adenine, ethanolamine, D-glucose, heparin, a buffering agent, hydrocortisone, lipoic acid, phenol red, phosphoethanolamine, putrescine, sodium pyruvate, triiodothyronine, thymidine, L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine, L-valine, N-acetyl-cysteine, biotin, choline chloride, D-Ca$^{++}$-pantothenate, folic acid, i-inositol, niacinamide, pyridoxine, riboflavin, thiamine, vitamin B12, Pluronic F68, recombinant insulin, a calcium salt, $CuSO_4$, $FeSO_4$, $FeCl_3$, $Fe(NO_3)_3$, KCl, a magnesium salt, a manganese salt, sodium acetate, NaCl, $NaHCO_3$, $Na_2HPO_4$, $Na_2SO_4$, a selenium salt, a silicon salt, a molybdenum salt, a vanadium salt, a nickel salt, a tin salt, $ZnCl_2$, $ZnSO_4$ or other zinc salts, wherein each ingredient is added in an amount which supports the cultivation of a cell in vitro.

The invention is also directed to a cell culture medium comprising ingredients selected from ethanolamine, D-glucose, HEPES, insulin, linoleic acid, lipoic acid, phenol red, PLURONIC F68, putrescine, sodium pyruvate, transferrin, L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine, L-valine, biotin, choline chloride, D-Ca$^{++}$-pantothenate, folic acid, i-inositol, niacinamide, pyridoxine, riboflavin, thiamine, vitamin B12, one or more calcium salts, $Fe(NO_3)_3$, KCl, one or more magnesium salts, one or more manganese salts, NaCl, $NaHCO_3$, $Na_2HPO_4$, one or more selenium salts, one or more vanadium salts and one or more zinc salts, wherein each ingredient is present in an amount which supports the suspension cultivation of a mammalian epithelial cell in vitro. The invention is also directed to such media which can optionally further comprise one or more supplements selected from the group consisting of one or more cytokines, heparin, one or more animal peptides, one or more yeast peptides and one or more plant peptides (most preferably one or more of rice, aloevera, soy, maize, wheat, pea, squash, spinach, carrot, potato, sweet potato, tapioca, avocado, barley, coconut and/or green bean, and/or one or more other plants), e.g., see international application no. PCT/US97/18255, published as WO 98/15614.

The media provided by the present invention can be protein-free, and can be a 1× formulation or concentrated as, for example, a 10×, 20×, 25×, 50×, 10×, 500×, or 1000× medium formulation.

The media of the invention can also be prepared in different forms, such as dry powder media ("DPM"), a granulated preparation (which requires addition of water, but not other processing, such as adjusting pH), liquid media or as media concentrates.

The basal medium that is a medium useful only for maintenance, but not for growth or production of product, can comprise a number of ingredients, including amino acids, vitamins, organic and inorganic salts, sugars and other components, each ingredient being present in an amount which supports the cultivation of a mammalian epithelial cell in vitro.

In the medium, methods, kit and composition of the present invention, the medium can be used to culture a variety of cells. Preferably, the medium is used to culture eukaryotic cells. More preferably, the medium is used to culture plant and/or animal cells. More preferably, the medium is used to culture mammalian cells, fish cells, insect cells, amphibian cells or avian cells. More preferably, the medium is used to culture mammalian cells. More preferably, the medium may be used to culture mammalian cells, including primary epithelial cells (e.g., keratinocytes, cervical epithelial cells, bronchial epithelial cells, tracheal epithelial cells, kidney epithelial cells and retinal epithelial cells) and established cell lines and their strains (e.g., 293 embryonic kidney cells, BHK cells, HeLa cervical epithelial cells and PER-C6 retinal cells, MDBK (NBL-1) cells, 911 cells, CRFK cells, MDCK cells, CapT cells, CHO cells, BeWo cells, Chang cells, Detroit 562 cells, HeLa 229 cells, HeLa S3 cells, Hep-2 cells, KB cells, LS180 cells, LS174T cells, NCI-H-548 cells, RPMI 2650 cells, SW-13 cells, T24 cells, WI-28 VA13, 2RA cells, WISH cells, BS-C-I cells, LLC-MK$_2$ cells, Clone M-3 cells, 1-10 cells, RAG cells, TCMK-1 cells, Y-1 cells, LLC-PK$_1$ cells, PK(15) cells, GH$_1$ cells, GH$_3$ cells, L2 cells, LLC-RC 256 cells, MH$_1$C$_1$ cells, XC cells, MDOK cells, VSW cells, and TH-I, B1 cells, or derivatives thereof), fibroblast cells from any tissue or organ (including but not limited to heart, liver, kidney, colon, intestines, esophagus, stomach, neural tissue (brain, spinal cord), lung, vascular tissue (artery, vein, capillary), lymphoid tissue (lymph gland, adenoid, tonsil, bone marrow, and blood), spleen, and fibroblast and fibroblast-like cell lines (e.g., CHO cells, TRG-2 cells, IMR-33 cells, Don cells, GHK-21 cells, citrullinemia cells, Dempsey cells, Detroit 551 cells, Detroit 510 cells, Detroit 525 cells, Detroit 529 cells, Detroit 532 cells, Detroit 539 cells, Detroit 548 cells, Detroit 573 cells, HEL 299 cells, IMR-90 cells, MRC-5 cells, WI-38 cells, WI-26 cells, MiCl$_1$ cells, CHO cells, CV-1 cells, COS-1 cells, COS-3 cells, COS-7 cells, Vero cells, DBS-FrhL-2 cells, BALB/3T3 cells, F9 cells, SV-T2 cells, M-MSV-BALB/3T3 cells, K-BALB cells, BLO-11 cells, NOR-10 cells, $C_3H/IOTI/2$ cells, $HSDM_1C_3$ cells, $KLN_2O_5$ cells, McCoy cells, Mouse L cells, Strain 2071 (Mouse L) cells, L-M strain (Mouse L) cells, L-MTK⁻ (Mouse L) cells, NCTC clones 2472 and 2555, SCC-PSA1 cells, Swiss/3T3 cells, Indian muntjac cells, SIRC cells, $C_{II}$ cells, and Jensen cells, or derivatives thereof). Most preferably, the medium is used to culture mammalian cells selected from the group consisting of 293 cells, 293 F cells or derivatives thereof, PER-C6 cells or derivatives thereof, CHO cells or derivatives thereof, CapT cells or derivatives thereof, COS-7L cells or derivatives thereof and Sp2/0 cells or derivatives thereof, or any other suspension cell line or derivative capable of being cultured at high cell density as defined above. More preferably, the medium is used to culture 293 cells or a modified 293 cell line specifically adapted for optimal growth in the cell culture medium that forms the basis of the present invention. In some preferred though non-limiting aspects, the medium is used to culture cells in suspension.

Cells supported by the medium of the present invention can be derived from any animal, preferably a mammal, and most preferably a mouse or a human. The cells cultivated in the present media can be normal cells or abnormal cells (i.e., transformed cells, established cells, or cells derived from diseased tissue samples).

The present invention also provides methods of cultivating mammalian epithelial or fibroblast cells using the culture medium formulations disclosed herein, comprising (a) contacting the cells with the cell culture media of the invention; and (b) cultivating the cells under conditions suitable to support cultivation of the cells. In some embodiments, the methods of the present invention can optionally include a step of contacting the cultured cells with a solution comprising one or more macromolecules (preferably comprising one or more nucleic acids) under conditions causing the introduction of one or more of the macromolecules into one or more of the cells. Preferably, cells cultivated according to these methods (which can include any of the cells described above) are cultivated in suspension.

In some aspects, a transient transfection and recombinant protein system may include a high density culture medium suitable for the growth and propagation of cultured mammalian cells at densities in the range of about $1\times10^6$ to about $20\times10^6$ cells/ml, more preferably in the range of about $2\times10^6$ to about $6\times10^6$. Any culture medium may be used in the practice of the present invention, with the proviso that the culture medium employed is capable of sustaining the growth of mammalian cells, preferably cells growing in suspension, at densities of up to about $2\times10^7$ cells/ml while maintaining viability of said cells in excess of about 80% and further, maintaining the ability of said suspension cells to be efficiently transfected and express high amounts of recombinant protein. The high density culture medium used in the practice of the present invention may vary between different applications and uses, and may depend on the nature of the cell line being used, the desired protein being transiently expressed, the nature of the transfection modality selected for transfer of the expression vector into cells, and the amount and nature of any expression enhancers added to the system as described below. Nevertheless, preferred high density culture medium contemplated for use in the present transient expression systems and methods will typically be serum-free, protein-free, allow the cultivation and growth of suspension cells to a density of up to about $2\times10^7$ cells/ml, more typically between about $2\times10^6$ cells/ml to about $1\times10^7$ cells/ml, and will further enable the yield of protein produced in the transient expression system to exceed at least 200 µg/mL of cell culture up to 2 mg/mL of cell culture, more typically between about 500 µg/ml of cell culture to about 1 mg/mL of cell culture. Ideally, the high density culture medium used in accordance with the present invention will facilitate the transfection of cells at densities in the range of about $1\times10^6$ to about $20\times10^6$ cells/ml, about $2\times10^6$ to about $2\times10^6$ cells/ml, or about $2.5\times10^6$ to about $6\times10^6$ cells/ml.

Particularly preferred high density growth media suitable for the practice of the present invention may be a chemically defined medium in which each chemical species and its respective quantity is known prior to its use in culturing cells. The selected chemically defined medium may optionally be made without cellular or tissue lysates or hydrolysates whose chemical species are not known and/or quantified.

In some aspects of the present invention a particularly suited type of medium for the practice of the present invention is a serum-free medium (sometimes referred to as "SFM Medium") being entirely devoid of, e.g., fetal bovine serum (FBS), calf serum, horse serum, goat serum, human serum, and the like. Exemplary though non-limiting serum-free media familiar to the skilled artisan include HuMEC Basal Serum free Medium, KNOCKOUT™ CTS™ Xeno-FREE ESC/iPSC Medium, STEMPRO™-34 SFM Medium, STEMPRO™ NSC Medium, ESSENTIAL™-8 Medium, Medium 254, Medium, 106, Medium, 131, Medium, 154, Medium, 171, Medium 171, Medium 200, Medium 231, HeptoZYME-SFM, Human Endothelial-SFM, GIBCO® FREESTYLE™ 293 Expression Medium, Medium 154CF/PRF, Medium 154C, Medium 154 CF, Medium 106, Medium 200PRF, Medium 131, Essential™-6 Medium, STEMPRO™-34 Medium, Gibco® Astrocyte Medium, AIM V® Medium CTS™, AMINOMAX™ C-100 Basal Medium, AMINOMAX™-II Complete Medium, CD FORTICHO™ Medium, CD CHO AGT Medium, CHO-S-SFM Medium, GIBCO®FREESTYLE™ CHO Expression Medium, CD OPTICHO™ Medium, CD CHO Medium, CD DG44 Medium, SF-900™ Medium, EXPI293™ Expression Medium, LHC Basal Medium, LHC-8 Medium, 293 SFM Medium, CD 293 Medium, AEM Growth Medium, PER.C6® Cell Medium, AIM V® Medium, EXPILIFE® Medium, Keratinocyte-SFM Medium, LHC Medium, LHC-8 Medium, LHC-9 Medium, and any derivatives or modifications thereof.

In some aspects of the present invention a particularly suited type of medium for the practice of the present invention is a protein-free medium (sometimes referred to as "PFM Medium") being entirely devoid of protein (e.g., no serum proteins such as serum albumin or attachment factors, nutritive proteins such as growth factors, or metal ion carrier proteins such as transferrin, ceruloplasmin, etc.). Preferably, if peptides are present, the peptides are smaller peptides, e.g., di- or tri-peptides. Preferably, peptides of deca-peptide length or greater are less than about 1%, more preferably less than about 0.1%, and even more preferably less than about 0.01% of the amino acids present in the protein free medium.

Ideally, both serum-free and protein-free media contemplated for use with the present invention will further be devoid of any animal derived material, or any material that is derived in whole or in part from an animal source, including recombinant animal DNA or recombinant animal protein DNA.

Exemplary high density culture media suitable for use in the practice of the present invention include, though are not limited to, HuMEC Basal Serum free Medium, KNOCK- OUT™ CTS™ XenoFREE ESC/iPSC Medium, STEMPRO™-34 SFM Medium, STEMPRO™ NSC Medium, ESSENTIAL™-8 Medium, Medium 254, Medium, 106, Medium, 131, Medium, 154, Medium, 171, Medium 171, Medium 200, Medium 231, HeptoZYME-SFM, Human Endothelial-SFM, GIBCO® FREESTYLE™ 293 Expression Medium, Medium 154CF/PRF, Medium 154C, Medium 154 CF, Medium 106, Medium 200PRF, Medium 131, Essential™-6 Medium, STEMPRO™-34 Medium, Gibco® Astrocyte Medium, AIM V® Medium CTS™, AMINOMAX™ C-100 Basal Medium, AMINOMAX™-II Complete Medium, CD FORTICHO™ Medium, CD CHO AGT Medium, CHO-S-SFM Medium, GIBCO®FREESTYLE™ CHO Expression Medium, CD OPTICHO™ Medium, CD CHO Medium, CD DG44 Medium, SF-900™ Medium, LHC Basal Medium, LHC-8 Medium, 293 SFM Medium, CD 293 Medium, AEM Growth Medium, PER. C6® Cell Medium, AIM V® Medium, EXPILIFE® Medium, Keratinocyte-SFM Medium, LHC Medium, LHC-8 Medium, LHC-9 Medium, and any derivatives or modifications thereof. In certain preferred though non-limiting embodiments, a high density culture media may be CD FORTICHO™ Medium, CD CHO AGT Medium, CHO-S-SFM Medium, GIBCO®FREESTYLE™ CHO Expression Medium, CD OPTICHO™ Medium, CD CHO Medium, CD DG44 Medium, GIBCO® FREESTYLE™ 293 Expression Medium, EXPI293™ Expression Medium, or a like medium, or a modified version thereof. The above listed exemplary high density culture media may be particularly suitable for the high density growth, propagation, transfection and maintenance of CHO cells, a CHO cell variant, 293 cells, a 293 cell variant, CapT cells, a CapT cell variant, or any other cells adapted for use in a high density culture system. Optionally, a user may wish to formulate a new culture medium having the properties described herein, or may opt instead to reformulate or modify existing culture media.

In some aspects, a high density growth medium may be selected from the list Such media include, but are not limited to, CD FORTICHO™ Medium, Expi293™ Expression Media, Dulbecco's Modified Eagle's Medium (DMEM), Minimal Essential Medium (MEM), Basal Medium Eagle (BME), RPMI-1640, Ham's F-10, Ham's F-12, α-Minimal Essential Medium (α-MEM), Glasgow's Minimal Essential Medium (G-MEM), and Iscove's Modified Dulbecco's Medium (IMDM). Other media that are commercially available (e.g., from Life Technologies Corporation, Carlsbad, Calif.) or that are otherwise known in the art can be equivalently used in accordance with the present invention including, but not limited to, 293 SFM, CD-CHO medium, VP SFM, BGJb medium, Brinster's BMOC-3 medium, cell culture freezing medium, CMRL media, EHAA medium, eRDF medium, Fischer's medium, Gamborg's B-5 medium, GLUTAMAX™ supplemented media, Grace's insect cell media, HEPES buffered media, Richter's modified MEM, IPL-41 insect cell medium, Leibovitz's L-15 media, McCoy's 5A media, MCDB 131 medium, Media 199, Modified Eagle's Medium (MEM), Medium NCTC-109, Schneider's *Drosophila* medium, TC-100 insect medium, Waymouth's MB 752/1 media, William's Media E, protein free hybridoma medium II (PFHM II), AIM V media, Keratinocyte SFM, defined Keratinocyte SFM, STEM-PRO® SFM, STEMPRO® complete methylcellulose medium, HepatoZYME-SFM, Neurobasal™ medium, Neurobasal-A medium, Hibernate™ A medium, Hibernate E medium, Endothelial SFM, Human Endothelial SFM, Hybridoma SFM, PFHM II, Sf 900 medium, Sf 900 TI SFM, EXPRESS FIVE® medium, CHO-S-SFM, AMINOMAX-II complete medium, AMINOMAX-C100 complete medium, AMINOMAX-C 100 basal medium, PB-MAX™ karyotyping medium, KARYOMAX bone marrow karyotyping medium, KNOCKOUT D-MEM and $CO_2$ independent medium. The above media are obtained from manufacturers known to those of ordinary skill in the art, such as JRH, Sigma, HyClone, and BioWhittaker. Additional examples of media suitable for use in the practice of the present invention can be found in U.S. Pat. Nos. 5,135,866 and 5,232,848 as well as in international publications nos. WO 88/02774, WO 98/15614, WO 98/08934 and European Patent No. 0 282 942, the entireties of which are specifically incorporated herein by reference. Optionally, a user may wish to formulate a new culture medium having the properties described herein, or may opt instead to reformulate or modify existing culture media.

The invention further provides compositions comprising the culture media of the present invention, which optionally can further comprise one or more mammalian epithelial or fibroblast cells, such as those described above, particularly one or more 293 cells, 293 F cells, PER-C6 cells, CHO cells, CapT cells, COS-7L cells and Sp2/0 cells, or any derivatives thereof.

In some aspects of the invention, the high yield transient transfection system of the present invention may include one or more cells or cell lines that are or have been adapted to grow under high density condition without substantial loss in their viability, ability to be efficiently transfected, or their ability to express high levels of recombinant protein. Preferably, a cell are cell line suitable for use in the present invention growth and propagation of cultured mammalian cells at densities in the range of about $1 \times 10^6$ to about $20 \times 10^6$ cells/ml, more preferably in the range of about $2 \times 10^6$ to about $6 \times 10^6$. Any cell line may be used, without limitation, provided the cell line are capable of growing under high density conditions as defined above, while maintaining their viability at high density in excess of about 80%, and retaining their ability to transfect at high efficiency and express recombinant protein at levels up to about 2 g/L of culture. The identification of such a cell line is well within the purview of the skilled artisan, and such a person can identify a suitable cell line for use in the present invention without departing from the spirit and scope thereof. The cells adapted for high density culture may be a cell lineage or a (non-clonal) population of cells derived from the same parental cell lineage which have been adapted to grow at high density in a high density culture medium while retaining cell viability at or above about 80%. Such cells may be isolated or selected out from the parental population of cells by maintaining the cells at high density over >40, >50, >60, >70, or >80 sequential passages and gradually replacing the proportion of growth medium with the desired high density culture medium. Optionally, during the process, different pools of cells may be individually propagated and subjected to the selection procedure while simultaneously assessing transfection efficiency and or protein expression efficiency, so that non-clonal population of cells may be selected that can be sustained and grown at high density, transfected with high efficiency, and express high levels of a desired recombinant protein. While it will be readily apparent to the skilled practitioner that a variety of cell types and lineages may be subjected to this selection procedure, it has been determined that cell lineages derived from CHO cells, cell lineages derived from 293 fibroblast cells, and cells derived from CapT cells are particularly amenable to the selection process for being adapted to high density growth conditions. Ideally, cells that are adapted to high density growth culture and amenable for use in the present invention will also be capable of being transfected at high efficiency and/or capable of expressing recombinant protein at yield exceeding at least 200 about µg/mL of cell culture up to about 2 mg/mL of cell culture, more typically between about 500 µg/ml of cell culture to about 1 mg/mL of cell culture. Ideally, cells adapted for high density culture used in accordance with the present invention are capable of being sustained and transfected at densities in the range of about $1 \times 10^6$ to about $20 \times 10^6$ cells/ml, about $2 \times 10^6$ to about $2 \times 10^6$ cells/ml, or about $2.5 \times 10^6$ to about $6 \times 10^6$ cells/ml.

By way of non-limiting example, cells or cell lines that may be adapted for high density culture according to the embodiments described herein may include cell such as cultured eukaryotic cells, more preferably, cultured plant and/or animal cells, more preferably, cultured mammalian cells, fish cells, insect cells, amphibian cells or avian cells. In certain preferred though non limiting embodiments, cells or cell lines that may be adapted for high density culture according to the embodiments described herein may include culture mammalian cells, including primary epithelial cells (e.g., keratinocytes, cervical epithelial cells, bronchial epithelial cells, tracheal epithelial cells, kidney epithelial cells and retinal epithelial cells) and established cell lines and their strains (e.g., 293 embryonic kidney cells, BHK cells, HeLa cervical epithelial cells and PER-C6 retinal cells, MDBK (NBL-1) cells, 911 cells, CRFK cells, MDCK cells, CapT cells, CHO cells, BeWo cells, Chang cells, Detroit 562 cells, HeLa 229 cells, HeLa S3 cells, Hep-2 cells, KB cells, LS180 cells, LS174T cells, NCI-H-548 cells, RPMI 2650 cells, SW-13 cells, T24 cells, WI-28 VA13, 2RA cells, WISH cells, BS-C-I cells, LLC-MK$_2$ cells, Clone M-3 cells, 1-10 cells, RAG cells, TCMK-1 cells, Y-1 cells, LLC-PK$_1$ cells, PK(15) cells, GH1 cells, GH$_3$ cells, L2 cells, LLC-RC 256 cells, MH$_1$C$_1$ cells, XC cells, MDOK cells, VSW cells, and TH-I, B1 cells, or derivatives thereof), fibroblast cells from any tissue or organ (including but not limited to heart, liver, kidney, colon, intestines, esophagus, stomach, neural tissue (brain, spinal cord), lung, vascular tissue (artery, vein, capillary), lymphoid tissue (lymph gland, adenoid, tonsil, bone marrow, and blood), spleen, and fibroblast and fibroblast-like cell lines (e.g., CHO cells, TRG-2 cells, IMR-33 cells, Don cells, GHK-21 cells, citrullinemia cells, Dempsey cells, Detroit 551 cells, Detroit 510 cells, Detroit 525 cells, Detroit 529 cells, Detroit 532 cells, Detroit 539 cells, Detroit 548 cells, Detroit 573 cells, HEL 299 cells, IMR-90 cells, MRC-5 cells, WI-38 cells, WI-26 cells, MiCl$_1$ cells, CHO cells, CV-1 cells, COS-1 cells, COS-3 cells, COS-7 cells, Vero cells, DBS-FrhL-2 cells, BALB/3T3 cells, F9 cells, SV-T2 cells, M-MSV-BALB/3T3 cells, K-BALB cells, BLO-11 cells, NOR-10 cells, C$_3$H/IOTI/2 cells, HSDM$_1$C$_3$ cells, KLN$_2$O$_5$ cells, McCoy cells, Mouse L cells, Strain 2071 (Mouse L) cells, L-M strain (Mouse L) cells, L-MTK⁻ (Mouse L) cells, NCTC clones 2472 and 2555, SCC-PSA1 cells, Swiss/3T3 cells, Indian muntjac cells, SIRC cells, C$_{II}$ cells, and Jensen cells, or derivatives thereof). Most preferably, the medium is used to culture mammalian cells selected from the group consisting of 293 cells, 293 F cells or derivatives thereof, PER-C6 cells or derivatives thereof, CHO cells or derivatives thereof, CapT cells or derivatives thereof, COS-7L cells or derivatives thereof and Sp2/0 cells or derivatives thereof, or any other suspension cell line or derivative capable of being cultured at high cell density as defined above. More preferably, the medium is used to culture 293 cells or a modified 293 cell line specifically adapted for optimal growth in the cell culture medium that forms the basis of the present invention. In some preferred though non-limiting aspects of the present invention, the cells adapted for use in high-density culture are suspension cells, or adherent cells that have been adapted to grow in suspension.

Cells supported by the medium of the present invention can be derived from any animal, preferably a mammal, and most preferably a mouse or a human. The cells cultivated in the present media can be normal cells or abnormal cells (i.e., transformed cells, established cells, or cells derived from diseased tissue samples).

Cells adapted to high density cultured in accordance with the embodiments described herein may optionally express one or more expression-enhancing proteins. As used herein, the term "expression enhancing protein" refers to any protein expressed by a cell; the expression of the protein enhances the expression of a recombinant protein. The expression of an expression-enhancing protein by a cell line or populations of cells may be stable or transient, for the purposes of the present embodiments. A variety of such expression-enhancing proteins are known in the art, and may include proteins such as, e.g., PKBa, Bcl-x$_L$, P21, P18, AKT, and the like. In some aspects of the invention, the high yield transient transfection system of the present invention may include one or more expression vectors for transiently expressing a recombinant protein of interest. The expression vector may be provided already containing an expressible nucleic acid (such as, e.g., a positive control to assess expression efficiency when compared to an optimized control protein), or alternatively, the expression vector may be provided in a form whereby the user may easily insert an expressible nucleic acid containing an open-reading frame of a protein of interest, such that the protein of interest can be expressed recombinantly and at high efficiency in the cells.

For recombinant production of a protein of interest, an expressible nucleic acid encoding the protein is isolated and inserted into a replicable vector for further cloning (amplification of the DNA) or for expression. DNA encoding the protein may be readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence.

a) Signal Sequence Component

A protein of interest may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. In mammalian cell expression, mammalian signal sequences as well as viral secretory leaders, for example, the herpes simplex gD signal, are available.

b) Origin of Replication

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2 plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

c) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up antibody-encoding nucleic acid, such as DHFR, glutamine synthetase (GS), thymidine kinase, metallothionein-I and -II, preferably primate metallothionein genes, adenosine deaminase, ornithine decarboxylase, etc.

For example, cells transformed with the DHFR gene are identified by culturing the transformants in a culture medium containing methotrexate (Mtx), a competitive antagonist of DHFR. Under these conditions, the DHFR gene is amplified along with any other co-transformed nucleic acid. A Chinese hamster ovary (CHO) cell line deficient in endogenous DHFR activity (e.g., ATCC CRL-9096) may be used.

Alternatively, cells transformed with the GS gene are identified by culturing the transformants in a culture medium containing L-methionine sulfoximine (Msx), an inhibitor of GS. Under these conditions, the GS gene is amplified along with any other co-transformed nucleic acid. The GS selection/amplification system may be used in combination with the DHFR selection/amplification system described above.

Alternatively, host cells (particularly wild-type hosts that contain endogenous DHFR) transformed or co-transformed with DNA sequences encoding an antibody of interest, wild-type DHFR gene, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., Nature, 282:39 (1979)). The trp1 gene provides a selection marker for a mutant strain of yeast lacking the ability to grow in tryptophan, for example, ATCC No. 44076 or PEP4-1. Jones, Genetics, 85:12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 µm circular plasmid pKD1 can be used for transformation of *Kluyveromyces* yeasts. Alternatively, an expression system for large-scale production of recombinant calf chymosin was reported for *K. lactis*. Van den Berg, Bio/Technology, 8:135 (1990). Stable multi-copy expression vectors for secretion of mature recombinant human serum albumin by industrial strains of *Kluyveromyces* have also been disclosed. Fleer et al., Bio/Technology, 9:968-975 (1991).

d) Promoter Component

Expression and cloning vectors generally contain a promoter that is recognized by the host organism and is operably linked to nucleic acid encoding a protein of interest. A variety of promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Protein transcription from vectors in mammalian host cells can be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus, Simian Virus 40 (SV40), or from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., Nature 297:598-601 (1982) on expression of human β-interferon cDNA in mouse cells under the control of a thymidine kinase promoter from herpes simplex virus. Alternatively, the Rous Sarcoma Virus long terminal repeat can be used as the promoter.

e) Enhancer Element Component

Transcription of a DNA encoding a protein of interest in accordance with the present invention by higher eukaryotes is often increased or enhanced by inserting an enhancer sequence into the vector. Many enhancer sequences are now known from mammalian genes (globin, elastase, albumin, α-fetoprotein, and insulin). Often, though not exclusively, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer may be spliced into the vector at a position 5' or 3' to the antibody-encoding sequence, but is preferably located at a site 5' from the promoter. Additional enhancers are known in art, and may include, for example, enhancers obtained or derived from mammalian or viral genes. One particularly preferred enhancers contemplated for use herein is the woodchuck hepatitis post-transcriptional regulatory element (WPRE).

f) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding antibody. One useful transcription termination component is the bovine growth hormone polyadenylation region. See WO94/11026 and the expression vector disclosed therein.

In some aspects, an expression vector well-suited for the practice of the present invention may be any of the well-known vectors used in the art, such as, e.g., pCDNA 3.3, or a modified version thereof. Non-limiting examples of the types of modification to a vector that may be suitable in the practice of the present invention include, though are not limited to, modification such as the addition of modification of one or more enhancers, one or more promoters, one or more ribosomal binding sites, one or more origins of replication, or the like. In certain preferred though non-limiting embodiments, and expression vector used in the practice of the present invention may include one or more enhancer elements selected to improve expression of the protein of interest in the present transient expression system. The selected enhancer element may be positioned 5' or 3' to the expressible nucleic acid sequence used to express the protein of interest. A particularly preferred though non-limiting enhancer element is the woodchuck hepatitis post-transcriptional regulatory element (WPRE).

In one preferred though non-limiting embodiment, an expression vector used in accordance with the presently described invention may be a pcDNA vector, or particularly, a pcDNA 3.3 vector, more particularly a variant of a pcDNA 3.3 vector. The vector may optionally include an enhanced promoter, such as, e.g., and enhanced CMV promoter. Optionally, the vector may include an Adeno T+M region, optionally an SV40ori site, optionally an SV40 splice donor/acceptor site, or optionally a woodchuck hepatitis post-transcriptional regulatory element (WPRE).

In some aspects of the invention, the high yield transient transfection system of the present invention may include one or more expression enhancers. An expression enhancer can be an aqueous solution containing one or more compounds that increase expression of a recombinant protein in a transient expression system. A variety of expression enhancers are known in the art, and any one or more may be used in the practice of the present invention without limitation.

Generally, the one or more transfection enhancers are contacted with a population of protein-expressing cells during or after said cells have been transfected with an expressible nucleic acid or expression vector. When two or more expression enhancer are used, each expression enhancer may be contacted with the cells at substantially the same time, or alternatively the expression enhancers may be contacted with the protein-expressing cells sequentially, optionally after a period of time has passed between contacting the cells with a first expression enhancer and contacting the cells with a second expression enhancer.

While it will be readily appreciated by the skilled artisan that any number of expression enhancers may be used in the practice of the present invention, without limitation, and the identification of what constitutes a suitable expression enhancer for use in the present embodiments is well within the purview of such a person, a variety of exemplary though non-limiting expression enhancers will be described below, though it is to be understood that the recitation thereof does not limit the scope of suitable expressions that may be contemplated for use in the practice of the present invention.

In some aspects, one or more expression enhancers may include liquid (preferably aqueous) additives used to supplement a culture medium formulation in accordance with the presently described embodiments, said additives being selected to improve the yield of expressed protein produced in a transient protein expression system in accordance with the presently described embodiments. One or more expression enhancers may include one or more of several compounds that impact cell cycle progression, inhibit apoptosis, slow cell growth and/or promote protein production. In the context of the present invention, the term "expression enhancers" generally refers to any one or more compounds added to a transient transfection system, the presence of which enhances or promotes expression of a target protein by a factor of at least 2 fold up to about 10-fold above the expression level seen in the absence of such expression enhancer(s). Exemplary expression enhancers suitable for use with the presently described embodiments include, though are not limited to, additives such as valproic acid (VPA, acid and sodium salt), sodium propionate, lithium acetate, dimethyl sulfoxide (DMSO), sugars including galactose, amino acid mixtures, or butyric acid, or any combinations of the aforementioned. The optimal concentration of each specific expression enhancer may vary according to individual characteristics of the expression system and the requirements of the user, and the determination of what constitutes an optimal concentration of any one or more expression enhancer in a given experimental scenario is well within purview of a practitioner having ordinary skill level in the art.

In one exemplary embodiment, an expression enhancer can be a formulation containing valproic acid. The optimal final concentration ranges of valproic acid (VPA) used in the practice of the present invention may vary, but will preferably be in the range of about 0.20 mM to about 25 mM, or any sub-ranges or concentration values encompassed by this range. More preferably, the final concentration of VPA may be in the range of about 0.25 mM to about 24 mM, about 0.26 mM to about 23 mM, 0.27 mM to about 23 mM, 0.28 mM to about 23 mM, 0.29 mM to about 22 mM, about 0.30 mM to about 21 mM, about 0.31 mM to about 20 mM, about 0.32 mM to about 19 mM, about 0.33 mM to about 17 mM, about 0.34 mM to about 18 mM, about 0.35 mM to about 17 mM, about 0.36 mM to about 16 mM, about 0.37 mM to about 15 mM, about 0.40 mM to about 14 mM, about 0.41 mM to about 13 mM, about 0.42 mM to about 12 mM, about 0.43 mM to about 11 mM, about 0.44 mM to about 10 mM, about 0.45 mM to about 9 mM, about 0.46 mM to about 8 mM, about 0.47 mM to about 7 mM, about 0.48 mM to about 6 mM, about 0.49 mM to about 5 mM, about 0.50 mM to about 4 mM, about 0.50 mM to about 4 mM, about 0.55 mM to about 3 mM, 0.6 mM to about 2 mM or 0.75 to about 1.5 mM. In some preferred though non-limiting embodiments, the final concentration of VPA used in the practice of the present invention may be between about 0.15 mM to about 1.5 mM, about 0.16 mM to about 1.5 mM, about 0.17 mM to about 1.5 mM, about 0.18 mM to about 1.5 mM, about 0.19 mM to about 1.5 mM, about 0.20 mM to about 1.5 mM, about 0.25 mM to about 1.5 mM, about 0.30 mM to about 1.5 mM, about 0.40 mM to about 1.5 mM, about 0.50 mM to about 1.5 mM, about 0.60 mM to about 1.5 mM, about 0.70 mM to about 1.5 mM, about 0.80 mM to about 1.5 mM, about 0.90 mM to about 1.5 mM or about 0.10 mM to about 1.5 mM. In some preferred though non-limiting embodiments, the final concentration of VPA used in the practice of the present invention may be between about 0.20 to about 1.5 mM, about 0.21 to about 1.4 mM, about 0.22 to about 1.4 mM, about 0.23 to about 1.4 mM, about 0.24 to about 1.4 mM, about 0.25 to about 1.3 mM, about 0.25 to about 1.2 mM, about 0.25 to about 1.1 mM, or about 0.25 to about 1.0 mM.

In another exemplary embodiment, an expression enhancer can be a formulation containing sodium propionate (NaPP). Optionally, NaPP may be provided alone or in combination with valproic acid as above. The optimal final concentration ranges of NaPP used in the practice of the present invention may vary, but will preferably be in the range of about In further embodiments, the optimal final concentration of NaPP used in the practice of the present invention may be in the range of about 0.2 mM to about 100 mM, or any sub-range or individual concentration encompassed within this range. In certain preferred though non-limiting embodiments, the optimal final concentration of NAPP may be in the range of about 0.5 to about 80 mM, about 0.4 mM to about 70 mM, about 0.5 mM to about 60 mM, about 0.6 mM to about 50 mM, about 0.7 mM to about 40 mM, about 0.8 mM to about 30 mM, about 0.9 mM to about 20 mM, about 1 mM to about 15 mM, about 2 mM to about 10 mM, about 3 mM to about 9 mM, about 4 mM to about 8 mM, or about 5 mM to about 7 mM. In certain preferred though non-limiting embodiments, the optimal final concentration of NAPP may be in the range of about 1 mM to about 10 mM, about 1 mM to about 2 mM, about 2 mM to about 3 mM, about 3 mM to about 4 mM, about 4 mM to about 5 mM, about 5 mM to about 6 mM, about 6 mM to about 7 mM, about 7 mM to about 8 mM, about 8 mM to about 9 mM, or about 9 mM to about 10 mM. In certain preferred though non-limiting embodiments, the optimal final concentration of NAPP may be about 1 mM, about 1.5 mM, about 2 mM, about 2.5 mM, about 3 mM, about 3.5 mM, about 4 mM, about 4.5 mM, about 5 mM, about 5.5 mM, about 6 mM, about 6.5 mM, about 7 mM, about 7.5 mM, about 8 mM, about 8.5 mM, about 9 mM, about 9.5 mM, or about 10 mM.

In yet another exemplary embodiment, an expression enhancer can be a formulation containing lithium acetate (LiAc). Optionally, LiAc may be provided alone or in combination with NaPP or valproic acid as above. In further embodiments, the optimal final concentration of lithium acetate (LiAc) used in the practice of the present invention may be in the range of about 0.25 to about 25 mM, about 0.26 mM to about 20 mM, about 0.27 mM to about 15 mM, about 0.28 mM to about 10 mM, about 0.29 mM to about 5 mM, about 0.3 mM to about 4.5 mM, about 0.31 mM to about 4 mM, about 0.35 mM to about 3 mM, about 0.5 mM to about 2.5 mM, about 1 mM to about 3 mM, about 1.5 mM to about 2.5 mM, or about 2 mM to about 3 mM.

In yet another exemplary embodiment still, an expression enhancer can be a formulation containing butyric acid. The optimal final concentration of butyric acid used in the practice of the present invention may be in the range of about 0.25 to about 25 mM, about 0.26 mM to about 20 mM, about 0.27 mM to about 15 mM, about 0.28 mM to about 10 mM, about 0.29 mM to about 5 mM, about 0.3 mM to about 4.5 mM, about 0.31 mM to about 4 mM, about 0.35 mM to about 3 mM, about 0.5 mM to about 2.5 mM, about 1 mM to about 3 mM, about 1.5 mM to about 2.5 mM, or about 2 mM to about 3 mM.

An expression enhancer used in accordance with the present invention may be added to the culture medium immediately prior to or during transfection, or after transfection but prior to harvesting the cells and the expressed protein. In some specific though non-limiting embodiments described below, "Enhancer 1" generally refers to 0.25 mM-1 mM valproic acid, and "Enhancer 2" generally refers to 5 mM-7 mM sodium propionate. However, if indicated otherwise, the terms Enhancer 1 and Enhancer 2 may encompass different enhancer compounds. Expression enhancers may be added to a culture medium sequentially, or as a cocktail.

In some aspects of the invention, the high yield transient transfection system of the present invention may include one or more reagents for the introduction of macromolecules into the cultured cells (said reagents being commonly referred to as "transfection reagents"). A transfection reagent used in accordance with the presently described embodiments can be any compound or other chemical modality for introducing a biological molecule, particularly a nucleic acid molecule, into a cell whereby the nucleic acid may exert a biological function, or in the case of an expressible nucleic acid, where a gene or protein encoded by said expressible nucleic acid can be expressed. A variety of suitable transfection reagents are known in the art, and any one or more may be used in the practice of the present invention without limitation.

A transfection reagent for use with the present embodiments is any formulation or composition known to those of skill in the art which facilitates the entry of a macromolecule into a cell. For example, see U.S. Pat. No. 5,279,833. In some embodiments, the reagent can be a "transfection reagent" and can be any compound and/or composition that increases the uptake of one or more nucleic acids into one or more target cells. A variety of transfection reagents are known to those skilled in the art. Suitable transfection reagents can include, but are not limited to, one or more compounds and/or compositions comprising cationic polymers such as polyethyleneimine (PEI), polymers of positively charged amino acids such as polylysine and polyarginine, positively charged dendrimers and fractured dendrimers, cationic β-cyclodextrin containing polymers (CD-polymers), DEAE-dextran and the like. In some embodiments, a reagent for the introduction of macromolecules into cells can comprise one or more lipids which can be cationic lipids and/or neutral lipids. Preferred lipids include, but are not limited to, N-[1-(2,3-dioleyloxy)propyl]-N,N,N-trimethylamonium chloride (DOTMA), dioleoylphosphatidylcholine (DOPE), 1,2-Bis(oleoyloxy)-3-(4'-trimethylammonio) propane (DOTAP), 1,2-dioleoyl-3-(4'-trimethylammonio) butanoyl-sn-glycerol (DOTB), 1,2-dioleoyl-3-succinyl-sn-glycerol choline ester (DOSC), cholesteryl (4'-trimethylammonio)butanoate (ChoTB), cetyltrimethylammonium bromide (CTAB), 1,2-dioleoyl-3-dimethyl-hydroxyethyl ammonium bromide (DORI), 1,2-dioleyloxypropyl-3-dimethyl-hydroxyethyl ammonium bromide (DORIE), 1,2-dimyristyloxypropyl-3-dimethyl-hydroxyethyl ammonium bromide (DMRIE), O,O'-didodecyl-N-[p(2-trimethylammonioethyloxy)benzoyl]-N, N,N-trimethylammonium chloride, spermine conjugated to one or more lipids (for example, 5-carboxyspermylglycine dioctadecylamide (DOGS), N,N$^I$,N$^{II}$,N$^{III}$-tetramethyl-N,N$^I$, N$^{II}$,N$^{III}$-tet-rapalmitylspermine (TM-TPS) and dipalmitoylphosphatidylethanolamine 5-carboxyspermylaminde (DPPES)), lipopolylysine (polylysine conjugated to DOPE), TRIS (Tris(hydroxymethyl)aminomethane, tromethamine) conjugated fatty acids (TFAs) and/or peptides such as trilysyl-alanyl-TRIS mono-, di-, and tri-palmitate, (3β-[N—(N', N'-dimethylaminoethane)-carbamoyl] cholesterol (DC- Chol), N-(α-trimethylammonioacetyl)-didodecyl-D-glutamate chloride (TMAG), dimethyl dioctadecylammonium bromide (DDAB), 2,3-dioleyloxy-N-[2(spermine-carboxamido)ethyl]-N,N-dimethyl-1-propanamin-iniumtrifluoroacetate (DOSPA) and combinations thereof.

Those skilled in the art will appreciate that certain combinations of the above mentioned lipids have been shown to be particularly suited for the introduction of nucleic acids into cells for example a 3:1 (w/w) combination of DOSPA and DOPE is available from Life Technologies Corporation, Carlsbad, Calif. under the trade name LIPOFECTAMINE™, a 1:1 (w/w) combination of DOTMA and DOPE is available from Life Technologies Corporation, Carlsbad, Calif. under the trade name LIPOFECTIN®, a 1:1 (M/M) combination of DMRIE and cholesterol is available from Life Technologies Corporation, Carlsbad, Calif. under the trade name DMRIE-C reagent, a 1:1.5 (M/M) combination of TM-TPS and DOPE is available from Life Technologies Corporation, Carlsbad, Calif. under the trade name CellFECTIN® and a 1:2.5 (w/w) combination of DDAB and DOPE is available from Life Technologies Corporation, Carlsbad, Calif. under the trade name LipfectACE®. In addition to the above-mentioned lipid combinations, other formulations comprising lipids in admixture with other compounds, in particular, in admixture with peptides and proteins comprising nuclear localization sequences, are known to those skilled in the art. For example, see international application no. PCT/US99/26825, published as WO 00/27795, both of which are incorporated by reference herein.

Lipid aggregates such as liposomes have been found to be useful as agents for the delivery of macromolecules into cells. In particular, lipid aggregates comprising one or more cationic lipids have been demonstrated to be extremely efficient at the delivery of anionic macromolecules (for example, nucleic acids) into cells. One commonly used cationic lipid is N-[1-(2,3-dioleoyloxy)propyl]-N,N,N-trimethylammonium chloride (DOTMA). Liposomes comprising DOTMA alone or as a 1:1 mixture with dioleoylphosphatidylethanolamine (DOPE) have been used to introduce nucleic acids into cells. A 1:1 mixture of DOTMA:DOPE is commercially available from Life Technologies Corporation, Carlsbad, Calif. under the trade name of LIPOFECTIN™. Another cationic lipid that has been used to introduce nucleic acids into cells is 1,2-bis(oleoyl-oxy)-3-3-(trimethylammonia) propane (DOTAP). DOTAP differs from DOTMA in that the oleoyl moieties are linked to the propylamine backbone via ether bonds in DOTAP whereas they are linked via ester bonds in DOTMA. DOTAP is believed to be more readily degraded by the target cells. A structurally related group of compounds wherein one of the methyl groups of the trimethylammonium moiety is replaced with a hydroxyethyl group are similar in structure to the Rosenthal inhibitor (RI) of phospholipase A (see Rosenthal, et al., (1960) J. Biol. Chem. 233:2202-2206.). The RI has stearoyl esters linked to the propylamine core. The dioleoyl analogs of RI are commonly abbreviated DOR1-ether and DOR1-ester, depending upon the linkage of the lipid moiety to the propylamine core. The hydroxyl group of the hydroxyethyl moiety can be further derivatized, for example, by esterification to carboxyspermine.

Another class of compounds which has been used for the introduction of macromolecules into cells comprise a carboxyspermine moiety attached to a lipid (see, Behr, et al., (1989) Proceedings of the National Academy of Sciences, USA 86:6982-6986 and EPO 0 394 111). Examples of compounds of this type include dipalmitoylphosphatidylethanolamine 5-carboxyspermylamide (DPPES) and 5-carboxyspermylglycine dioctadecylamide (DOGS). DOGS is commercially available from Promega, Madison, Wis. under the trade name of TRANSFECTAM™.

A cationic derivative of cholesterol (3β-[N—(N',N'-dimethylaminoethane)-carbamoyl]cholesterol, DC-Chol) has been synthesized and formulated into liposomes with DOPE (see Gao, et al., (1991) BBRC 179(1):280-285.) and used to introduce DNA into cells. The liposomes thus formulated were reported to efficiently introduce DNA into the cells with a low level of cellular toxicity. Lipopolylysine, formed by conjugating polylysine to DOPE (see Zhou, et al., (1991) BBA 1065:8-14), has been reported to be effective at introducing nucleic acids into cells in the presence of serum.

Other types of cationic lipids that have been used to introduce nucleic acids into cells include highly packed polycationic ammonium, sulfonium and phosphonium lipids such as those described in U.S. Pat. Nos. 5,674,908 and 5,834,439, and international application no. PCT/US99/26825, published as WO 00/27795. One particularly preferred though non-limiting transfection reagent for delivery of macromolecules in accordance with the present invention is LIPOFECTAMINE 2000™ which is available from Life technologies. See U.S. international application no. PCT/US99/26825, published as WO 00/27795. Another preferred though non-limiting transfection reagent suitable for delivery of macromolecules to a cell is EXPIFECTAMINE™. Other suitable transfection reagents include LIOFECTAMINE™ RNAiMAX, LIPOFECTAMINE™ LTX, OLIGOFECTAMINE™, Cellfectin™, INVIVOFECTAMINE™, INVIVOFECTAMINE™ 2.0, and any of the lipid reagents or formulations disclosed in U.S. Patent Appl. Pub. No. 2012/0136073, by Yang et al. (incorporated herein by reference thereto). A variety of other transfection reagents are known to the skilled artisan and may be evaluated for the suitability thereof to the transient transfection systems and methods described herein.

The present invention is directed, in part, to a high-yield transient transfection system that supports (a) the introduction of at least one macromolecule, preferably an expressible nucleic acid molecule, into eukaryotic cells in culture, (b) the cultivation of cells into which at least one macromolecule is introduced, and optionally (c) the production of recombinant protein product or expression of the nucleic acid in cells into which at least one macromolecule is introduced, wherein medium containing the macromolecule does not need to be removed from the culture and replaced with fresh medium after introduction of at least one macromolecule into cells and prior to cultivation and production of protein product or expression of nucleic acid. The transient transfection system of the present invention, an the use thereof in accordance with the methods described herein, results in the rapid and reproducible expression of high levels of a protein of interest in a cell culture system. Typically, the present transient transfection systems and methods are capable of producing recombinant expressed protein at levels in the range of about 200 µg protein/L of culture to about 2 g protein/L of culture, depending on the individual expression characteristics of the desired recombinant protein and cell type used. Using the transient transfection system and methods provided for herein, a user may obtain levels of expressed protein that are about 2-fold to up to about 20-fold in excess of what is currently obtainable using standard commercially available transient transfection systems. Using the transient transfection system and methods provided for herein, a user may obtain levels of expressed protein that is about 2.5-fold, about 3-fold, about 3.5-fold, about 4-fold, about 4.5-fold, about 5-fold, about 5.5-fold, about 6-fold, about 6.5-fold, bout 7-fold, about 7.5-fold, about 8-fold, about 8.5-fold, about 9-fold, about 9.5-fold, or up to about 10-fold or greater than that seen with contemporary transient expression systems. For example, using the present transient transfection system to produce a recombinant protein, a user may obtain a protein yield between about 2-fold up to about 10-fold higher than the protein yield obtained using a commercially available transient transfection system optimized for production of recombinant protein in suspension cells, such as, e.g., FREE-STYLE™ Expression System. Methods The present invention further relates to methods for expressing high levels of a protein of interest. Methods of the invention may include cultivating mammalian cells (particularly those described above and most particularly 293 cells, 293 F cells, PER-C6 cells, CHO cells, CapT cells, COS-7L cells and Sp2/0 cells, or any derivatives thereof) in suspension comprising (a) obtaining a mammalian cell to be cultivated in suspension; and (b) contacting the cell with the culture media of the invention under conditions sufficient to support the cultivation of the cell in suspension, transfecting the cultured cells with an expressible nucleic acid encoding a protein of interest, contacting the transfected cells with one or more expression enhancers, culturing the transfected cells under conditions permissive to the expression of the protein of interest for a defined period of time, and harvesting the cells.

The present invention further relates to methods of producing a polypeptide, and to polypeptides produced by these methods, the methods comprising (a) obtaining a cell, preferably a mammalian cell described above and most preferably a 293 cells, 293 F cells, PER-C6 cells, CHO cells, CapT cells, COS-7L cells and Sp2/0 cells, or any derivatives thereof; (b) contacting the cell with a solution comprising a nucleic acid encoding the polypeptide under conditions causing the introduction of the nucleic acid into the cell; and (c) cultivating the cell in the culture medium of the invention under conditions favoring the expression of the desired polypeptide by the cell.

In one aspect, a method for expressing a recombinant protein in according with the present invention may include obtaining a culture of cells in a high density culture medium. The cells are preferably a suspension culture of 293 cells, 293 F cells, PER-C6 cells, CHO cells, CapT cells, COS-7L cells or Sp2/0 cells, or any derivatives thereof, which cells have been adapted for growth in high density medium. While it will be readily appreciated by the skilled artisan that any volume of cell culture may be used in the practice of the present invention, the culture will typically be from about 200 µl to 100 liters, more preferably, the cell culture volume is from about 2 ml to about 50 liters, most preferably from about 5 ml to about 5 liters. In some aspects, the cell culture volume can be from about 100 ml to about 50 liters. More preferably, the cell culture volume is from about 500 ml to about 50 liters. More preferably, the cell culture volume is from about 500 ml to about 25 liters. More preferably, the cell culture volume is from about 500 ml to about 10 liters. More preferably, the cell culture volume is from about 500 ml to about 5 liters. More preferably, the cell culture volume is from about 500 ml to about 1 liter. In some embodiments, the cell culture volume can be up to about 100 liters, up to about 95 liters, up to about 90 liters, up to about 85 liters, up to about 80 liters, up to about 75 liters, up to about 70 liters, up to about 65 liters, up to about 60 liters, up to about 55 liters, up to about 50 liters, up to about 45 liters, up to about 40 liters, up to about 35 liters, up to about 30 liters, up to about 35 liters, up to about 20 liters, up to about 15 liters, up to about 10 liters, up to about 9 liters, up to about 8 liters, up to about 7 liters, up to about 6 liters, up to about 5 liters, up to about 4 liters, up to about 2 liters or up to about 1 liter.

In one aspect, the cell culture may be maintained at a cell density of between about $1.5 \times 10^6$ cells/ml to about $20 \times 10^6$ cells/ml, or any concentration, concentration range or sub-range encompassed therein.

To express a protein in cells in accordance with the presently described invention, the cells will typically be diluted into a fresh volume of medium. The optimal dilution can vary, though for illustrative purposes, the density of cells diluted into a fresh volume of medium can be between $0.5 \times 10^6$ cells/ml to about $10 \times 10^6$ cells/ml, more preferably $1 \times 10^6$ cells/ml to about $5 \times 10^6$ cells/ml, more preferably, $1.5 \times 10^6$ cells/ml to about $3 \times 10^6$ cells/ml.

In one aspect, following dilution of the cells into a fresh volume of culture medium, the cells can be cultured in said volume for a period of time, prior to being transfected with an expressible nucleic acid. Optionally, the cells can be cultured for up to 2 days, more preferably up to about a day and a half, most preferably, up to about a day. Optionally, the cells can be cultured in the fresh volume of medium until the density of the cells cultured therein has increased by up to about 100%, more preferably up to about 95%, up to about 90%, up to about 85%, up to about 80%, up to about 75%, up to about 70%, up to about 65%, up to about 60% up to about 55%, up to about 50%, up to about 45%, up to about 40%, up to about 35%, up to about 30%, up to about 25%, up to about 20% or up to about 15%.

In one aspect, cells may be transfected with an expressible nucleic acid or an expression vector after the cells have been cultured in the high density growth media for a period of time as described above. The precise sequence of steps a user undertakes to accomplish the introduction of the expression vector into the cells may vary, depending on the specific transfection reagent selected, the cell line, the media and various other experimental parameters, as will be readily recognized by a practitioner having ordinary skill level in the art. By way of example only, in the case where a lipid-based transfection system is selected (in particular, a transfection system having at least one cationic lipid), the transfection reagent will first be contacted with the nucleic acid in an aqueous solution to form lipid-DNA complexes in a process known informally as "complexation" or a "complexation reaction" as defined above and incorporated herein. Such a reaction will typically be accomplished in a separate reaction vessel from that in which the cells are being cultured.

In an aspect, following the formation of lipid-DNA complexes in the complexation step described above, the transfection complexes can be contacted with the cultured cells. After contacting the cells with the transfection complexes, the cells can be cultured in the presence of the transfection complexes for a first period of time. The duration of the first period of time will vary according to the nature of the cells, the transfection reagent used, and a variety of other factors know to those skilled in the art. The phrase "first period of time", when used in the context of a method for transiently transfecting cells in accordance with the methods of the invention described herein generally refers to the time interval between transfecting a population of cells with an expressible nucleic acid and the additional of one or more expression enhancers to the transfected cells. Typically, a first period of time will be in the range of about 2 hrs to about 4 days, or any ranges or sub-ranges encompassed therein. In certain preferred though non-limiting embodiments, a first period of time may be in the range of about 3 to about 90 hrs, about 4 to about 85 hr, about 5 to about 80 hrs, about 6 to about 75 hrs, about 7 to about 70 hrs, about 8 to about 65 hrs, about 9 to about 60 hrs, about 10 to about 55 hrs, about 11 to about 50 hrs, about 12 to about 45 hrs, about 13 to about 40 hrs, about 14 to about 35 hrs, about 15 to 30 hrs, about 16 to about 24 hrs, about 17 to about 24 hrs, about 18 to about 24 hrs, about 19 to about 24 hrs, about 20 to about 24 hrs, about 21 to about 24 hrs, about 22 to about 24 hrs or about 23 to about 24 hrs. In other preferred to non-limiting embodiments, a first period of time may be up to about 15 hrs, up to about 16 hrs, up to about 17 hrs, up to about 18 hrs, up to about 19 hrs, up to about 20 hrs, up to about 21 hrs, up to about 22 hrs, up to about 23 hrs, up to about 24 hrs, up to about 25 hrs, up to about 26 hrs, up to about 27 hrs, up to about 28 hrs, up to about 29 hrs or up to about 30 hrs.

In one highly preferred though non-limiting embodiment, the culture medium is not replaced, supplemented or replenished following the introduction of the transfection complexes to the cells, and for the duration of the first period of time.

In one aspect of the present invention, the transfected cells in culture may be contacted with one or more expression enhancers following the first period of time. An expression enhancer can be an aqueous solution containing one or more compounds that increase expression of a recombinant protein in a transient expression system. A variety of expression enhancers are known in the art, and any one or more may be used in the practice of the present invention without limitation.

Generally, the one or more transfection enhancers are contacted with a population of protein-expressing cells during or after said cells have been transfected with an expressible nucleic acid or expression vector. When two or more expression enhancer are used, each expression enhancer may be contacted with the cells at substantially the same time, or alternatively the expression enhancers may be contacted with the protein-expressing cells sequentially, optionally after a period of time has passed between contacting the cells with a first expression enhancer and contacting the cells with a second expression enhancer.

While it will be readily appreciated by the skilled artisan that any number of expression enhancers may be used in the practice of the present invention, without limitation, and the identification of what constitutes a suitable expression enhancer for use in the present embodiments is well within the purview of such a person, a variety of exemplary though non-limiting expression enhancers will be described below, though it is to be understood that the recitation thereof does not limit the scope of suitable expressions that may be contemplated for use in the practice of the present invention.

In some aspects, one or more expression enhancers may include liquid (preferably aqueous) additives used to supplement a culture medium formulation in accordance with the presently described embodiments, said additives being selected to improve the yield of expressed protein produced in a transient protein expression system in accordance with the presently described embodiments. One or more expression enhancers may include one or more of several compounds that impact cell cycle progression, inhibit apoptosis, slow cell growth and/or promote protein production. In the context of the present invention, the term "expression enhancers" generally refers to any one or more compounds added to a transient transfection system, the presence of which enhances or promotes expression of a target protein by a factor of at least 2 fold up to about 10-fold above the expression level seen in the absence of such expression enhancer(s). Exemplary expression enhancers suitable for use with the presently described embodiments include, though are not limited to, additives such as valproic acid (VPA, acid and sodium salt), sodium propionate, lithium acetate, dimethyl sulfoxide (DMSO), sugars including galactose, amino acid mixtures, or butyric acid, or any combinations of the aforementioned. The optimal concentration of each specific expression enhancer may vary according to individual characteristics of the expression system and the requirements of the user, and the determination of what constitutes an optimal concentration of any one or more expression enhancer in a given experimental scenario is well within purview of a practitioner having ordinary skill level in the art.

In one exemplary embodiment, an expression enhancer can be a formulation containing valproic acid. The optimal final concentration ranges of valproic acid (VPA) used in the practice of the present invention may vary, but will preferably be in the range of about 0.20 mM to about 25 mM, or any sub-ranges or concentration values encompassed by this range. More preferably, the final concentration of VPA may be in the range of about 0.25 mM to about 24 mM, about 0.26 mM to about 23 mM, 0.27 mM to about 23 mM, 0.28 mM to about 23 mM, 0.29 mM to about 22 mM, about 0.30 mM to about 21 mM, about 0.31 mM to about 20 mM, about 0.32 mM to about 19 mM, about 0.33 mM to about 17 mM, about 0.34 mM to about 18 mM, about 0.35 mM to about 17 mM, about 0.36 mM to about 16 mM, about 0.37 mM to about 15 mM, about 0.40 mM to about 14 mM, about 0.41 mM to about 13 mM, about 0.42 mM to about 12 mM, about 0.43 mM to about 11 mM, about 0.44 mM to about 10 mM, about 0.45 mM to about 9 mM, about 0.46 mM to about 8 mM, about 0.47 mM to about 7 mM, about 0.48 mM to about 6 mM, about 0.49 mM to about 5 mM, about 0.50 mM to about 4 mM, about 0.50 mM to about 4 mM, about 0.55 mM to about 3 mM, 0.6 mM to about 2 mM or 0.75 to about 1.5 mM. In some preferred though non-limiting embodiments, the final concentration of VPA used in the practice of the present invention may be between about 0.15 mM to about 1.5 mM, about 0.16 mM to about 1.5 mM, about 0.17 mM to about 1.5 mM, about 0.18 mM to about 1.5 mM, about 0.19 mM to about 1.5 mM, about 0.20 mM to about 1.5 mM, about 0.25 mM to about 1.5 mM, about 0.30 mM to about 1.5 mM, about 0.40 mM to about 1.5 mM, about 0.50 mM to about 1.5 mM, about 0.60 mM to about 1.5 mM, about 0.70 mM to about 1.5 mM, about 0.80 mM to about 1.5 mM, about 0.90 mM to about 1.5 mM or about 0.10 mM to about 1.5 mM. In some preferred though non-limiting embodiments, the final concentration of VPA used in the practice of the present invention may be between about 0.20 to about 1.5 mM, about 0.21 to about 1.4 mM, about 0.22 to about 1.4 mM, about 0.23 to about 1.4 mM, about 0.24 to about 1.4 mM, about 0.25 to about 1.3 mM, about 0.25 to about 1.2 mM, about 0.25 to about 1.1 mM, or about 0.25 to about 1.0 mM.

In another exemplary embodiment, an expression enhancer can be a formulation containing sodium propionate (NaPP). Optionally, NaPP may be provided alone or in combination with valproic acid as above. The optimal final concentration ranges of NaPP used in the practice of the present invention may vary, but will preferably be in the range of about In further embodiments, the optimal final concentration of NaPP used in the practice of the present invention may be in the range of about 0.2 mM to about 100 mM, or any sub-range or individual concentration encompassed within this range. In certain preferred though non-limiting embodiments, the optimal final concentration of NAPP may be in the range of about 0.5 to about 80 mM, about 0.4 mM to about 70 mM, about 0.5 mM to about 60 mM, about 0.6 mM to about 50 mM, about 0.7 mM to about 40 mM, about 0.8 mM to about 30 mM, about 0.9 mM to about 20 mM, about 1 mM to about 15 mM, about 2 mM to about 10 mM, about 3 mM to about 9 mM, about 4 mM to about 8 mM, or about 5 mM to about 7 mM. In certain preferred though non-limiting embodiments, the optimal final concentration of NAPP may be in the range of about 1 mM to about 10 mM, about 1 mM to about 2 mM, about 2 mM to about 3 mM, about 3 mM to about 4 mM, about 4 mM to about 5 mM, about 5 mM to about 6 mM, about 6 mM to about 7 mM, about 7 mM to about 8 mM, about 8 mM to about 9 mM, or about 9 mM to about 10 mM. In certain preferred though non-limiting embodiments, the optimal final concentration of NAPP may be about 1 mM, about 1.5 mM, about 2 mM, about 2.5 mM, about 3 mM, about 3.5 mM, about 4 mM, about 4.5 mM, about 5 mM, about 5.5 mM, about 6 mM, about 6.5 mM, about 7 mM, about 7.5 mM, about 8 mM, about 8.5 mM, about 9 mM, about 9.5 mM, or about 10 mM.

In yet another exemplary embodiment, an expression enhancer can be a formulation containing lithium acetate (LiAc). Optionally, LiAc may be provided alone or in combination with NaPP or valproic acid as above. In further embodiments, the optimal final concentration of lithium acetate (LiAc) used in the practice of the present invention may be in the range of about 0.25 to about 25 mM, about 0.26 mM to about 20 mM, about 0.27 mM to about 15 mM, about 0.28 mM to about 10 mM, about 0.29 mM to about 5 mM, about 0.3 mM to about 4.5 mM, about 0.31 mM to about 4 mM, about 0.35 mM to about 3 mM, about 0.5 mM to about 2.5 mM, about 1 mM to about 3 mM, about 1.5 mM to about 2.5 mM, or about 2 mM to about 3 mM.

In yet another exemplary embodiment still, an expression enhancer can be a formulation containing butyric acid. The optimal final concentration of butyric acid used in the practice of the present invention may be in the range of about 0.25 to about 25 mM, about 0.26 mM to about 20 mM, about 0.27 mM to about 15 mM, about 0.28 mM to about 10 mM, about 0.29 mM to about 5 mM, about 0.3 mM to about 4.5 mM, about 0.31 mM to about 4 mM, about 0.35 mM to about 3 mM, about 0.5 mM to about 2.5 mM, about 1 mM to about 3 mM, about 1.5 mM to about 2.5 mM, or about 2 mM to about 3 mM.

An expression enhancer used in accordance with the present invention may be added to the culture medium immediately prior to or during transfection, or after transfection but prior to harvesting the cells and the expressed protein. In some specific though non-limiting embodiments described below, "Enhancer 1" generally refers to 0.25 mM-1 mM valproic acid, and "Enhancer 2" generally refers to 5 mM-7 mM sodium propionate. However, if indicated otherwise, the terms Enhancer 1 and Enhancer 2 may encompass different enhancer compounds. Expression enhancers may be added to a culture medium sequentially, or as a cocktail.

In one aspect, when two or more expression enhancers are used, the two or more expression enhancers can be contacted with the transfected cultured cells substantially simultaneously, or alternatively the transfected cultured cells can first be contacted with a first expression enhancer, and after a second period of time, the transfected cultured cells can be contacted with the second expression enhancer. In one aspect, the "second period of time", when used in the context of a method for transiently transfecting cells in accordance with the methods of the invention described herein generally refers to the time interval between the addition of one or more expression enhancers and either the addition of one or more additional enhancers, or the harvesting of the transfected cells and purification or isolation of the protein expressed therein. Typically, a second period of time will be in the range of about 10 hrs to about 10 days, though other time intervals may be used if determined to be optimal for the protein being expressed. In some preferred though non-limiting embodiments, the second period of time may be in the range of 2 hrs to 5 days, 2.5 hrs to 4 days, about 3 to about 90 hrs, about 4 to about 85 hr, about 5 to about 80 hrs, about 6 to about 75 hrs, about 7 to about 70 hrs, about 8 to about 65 hrs, about 9 to about 60 hrs, about 10 to about 55 hrs, about 11 to about 50 hrs, about 12 to about 45 hrs, about 13 to about 40 hrs, about 14 to about 35 hrs, about 15 to 30 hrs, about 16 to about 24 hrs, about 17 to about 24 hrs, about 18 to about 24 hrs, about 19 to about 24 hrs, about 20 to about 24 hrs, about 21 to about 24 hrs, about 22 to about 24 hrs or about 23 to about 24 hrs. In other preferred to non-limiting embodiments, a first period of time may be up to about 15 hrs, up to about 16 hrs, up to about 17 hrs, up to about 18 hrs, up to about 19 hrs, up to about 20 hrs, up to about 21 hrs, up to about 22 hrs, up to about 23 hrs, up to about 24 hrs, up to about 25 hrs, up to about 26 hrs, up to about 27 hrs, up to about 28 hrs, up to about 29 hrs or up to about 30 hrs.

After an appropriate amount of time has elapsed, the user can harvest the cells and optionally purify the expressed recombinant protein.

The method of the present invention allows a user to transiently express a recombinant protein in accordance with the embodiments described above without having to replace, supplement or otherwise replenish the culture medium during the process. The methods described herein allow the user express up to about 2 g/L of cultured cells. In some embodiments, the user can express up to about 1.9 g, up to about 1.8 g, up to about 1.7 g, up to about 1.6 g, up to about 1.5 g, up to about 1.4 g, up to about 1.3 g, up to about 1.2 g, up to about 1.1 g, or up to about 1 g of recombinant protein for every liter of cultured cells.

The present invention is also directed to compositions, particularly a high density cell culture media as defined above, optionally comprising one or more replacement compounds. The invention is also directed to methods of use of such compositions, including, for example, methods for the cultivation of eukaryotic cells, particularly animal cells, in vitro. The invention also relates to compositions comprising such culture media and one or more cells, especially those cells specifically referenced herein, and to kits comprising one or more of the above-described compositions. The invention also relates to expression vectors comprising one or more expressible nucleic acid sequences in combination with one or more promoters, enhancers, and other elements required for expressing said expressible nucleic acid in a cultured cells, as defined above and incorporated herein. The invention also relates to compositions comprising one or more expression enhancer compositions, especially those selected to enhance expression of said expressible nucleic acid in a cultured cell by at least a factor or 2- to 2.5 fold. Optionally, the expression enhancers can be a combination of two or expression enhancers co-formulated or provided separately. The invention also relates to transfections reagents, especially those optimized to facilitate the delivery of one or more nucleic acid molecules to the interior of a cultured cell. The invention also relates to kits comprising one or more of the above-described compositions, vectors, expression enhancers, transfection reagents, and the like, and to kits comprising one or more of the above-described compositions, especially those cells specifically referenced herein.

In another aspect, the invention relates to a kit for the cultivation of cells in vitro. The kit comprise one or more containers, wherein a first container contains the culture medium of the present invention. The kit can further comprise one or more additional containers, each container containing one or more supplements selected from the group consisting of one or more cytokines, heparin, one or more animal or animal-derived peptides, one or more yeast peptides and one or more plant peptides (which are preferably one or more peptides from rice, aloevera, soy, maize, wheat, pea, squash, spinach, carrot, potato, sweet potato, tapioca, avocado, barley coconut and/or green bean, and/or one or more other plants).

The kit of the present invention can further comprise one or more containers comprising a nucleic acid and/or a reagent that facilitates the introduction of at least one macromolecule, e.g., a nucleic acid into cells cultured in the media of the present invention, i.e., a transfection reagent. Preferred transfection reagents include, but are not limited to, cationic lipids and the like.

A kit according to one aspect of the invention can comprise one or more of the culture media of the invention, one or more replacement compounds, which can be one or more metal binding compounds, and/or one or more transition element complexes, and can optionally comprise one or more nucleic acids and transfection reagents. Kits according to another aspect of the invention can comprise one or more cell culture media (one of which can be a basal medium) and optionally one or more replacement compounds. The kit of the present invention can also contain instructions for using the kit to culture cells and/or introduce macromolecules or compounds (e.g., nucleic acid, such as DNA), into cells.

It will be readily apparent to one of ordinary skill in the relevant arts that other suitable modifications and adaptations to the methods and applications described herein are obvious and can be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLES

Objectives:

To develop a cell culture medium and transfection system to maximize protein yields (at least 2-fold in excess of that obtained with commercially available transient expression systems, such as, e.g., Freestyle™ 293 system). The system should work for multiple protein types and in a variety of suspension cells. The system should increase reproducibility and minimize variability and should be scalable (multi-well plates to large scale). Further embodiments of the present invention include the development of an improved expression vector, a high density cell line adapted for growth under high density culture conditions in the culture system of the present invention, the use and incorporation of transfection enhancers such, for example, as valproic acid and sodium propionate (among others). It is a further object of the present invention to develop a protocol to enable transfection at high cell density, that does not involve media exchange during or after transfection, and that is simple and easy to use.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub combination.

Example 1: High Density Culture Medium

A variety of commercially available serum-free, protein-free culture media were assessed for their ability to sustain the viability of an adapted 293 F cell line with cell densities up to about $14 \times 10^6$ cells/ml and thus be used in the practice of the present invention. A serum-free, protein-free medium was selected wherein the viability of the culture cell line over a time frame exceeding a week remains high and even approached densities of nearly $15 \times 10^6$ cells/ml, while also enabling transfection at surprisingly high cell densities of around $3 \times 10^6$ cells/ml (vs. $1 \times 10^6$ cells/ml for present commercially available transient transfection systems). The results are depicted in FIG. 1, which shows a graph of the resulting cell densities that are achievable using the transient transfection system in accordance with some embodiments of the invention. Cells that were previously adapted for high density growth were slowly adapted into various tested growth media over 3 passages. The media to which the cells were adapted include High Density Culture Media in accordance with one embodiment of the invention (closed circles), Test Media 1 (closed triangles), Test Media 2 (open triangles), and Test Media 3 (open diamonds). Cells were cultured for multiple passages in each of the media before being seeded in 30 ml flasks at $0.2 \times 10^6$ cells/ml. Cell density and viability were monitored over 8 days without replenishing, replacing or otherwise supplementing the growth medium over the course of the experiment. One of the selected growth media (High Density Growth Medium; closed circles) was able to sustain a surprisingly high density of cultured suspension cells without substantially losing viability over the course of the experiment. Thus, it is possible for one skilled in the art to readily assess a variety of growth media for use with a specific cell line are variant of a cell line, where a growth medium can be selected based on the ability to facilitate the cultivation of high densities of suspension cells over a defined period of time, without having to replace, supplement or replenish the medium. Such may be accomplished by the skilled artisan without undue experimentation.

Example 2: Cell Line Optimization

Although a variety of suspension cells can be used in the practice of the present invention, it is preferable to use a cell line that has been adapted for use with the present embodiments and in the selected high density growth medium. Additionally, the cells may be specifically selected for high density growth, high viability, and increased protein expression. To accomplish this, parental 293F fibroblast cells underwent an extensive adaptation process involving gradual media replacement over several passages. Additionally, it was noted that the adapted cells' size and expression ability increased with subsequent generations. At passage 72, cells were banked and validated through genetic analysis at ATCC, and were authenticated as 293F cells with no mycoplasma contamination. The cells were thawed and their viability was verified. The cells were passaged for 30 passages to verify stability, expression performance, and their ability to retain high viability when grown in culture and densities of up to about $20 \times 10^6$ cells/ml. Cell populations selected for increased cell density, viability, and human IgG expression as described above exhibited approximately 1.7-fold more hIgG than the original cell line (Line 1). High yield adapted cells (Line 3) also have increased growth rate, viability and cell size.

Figure 2:
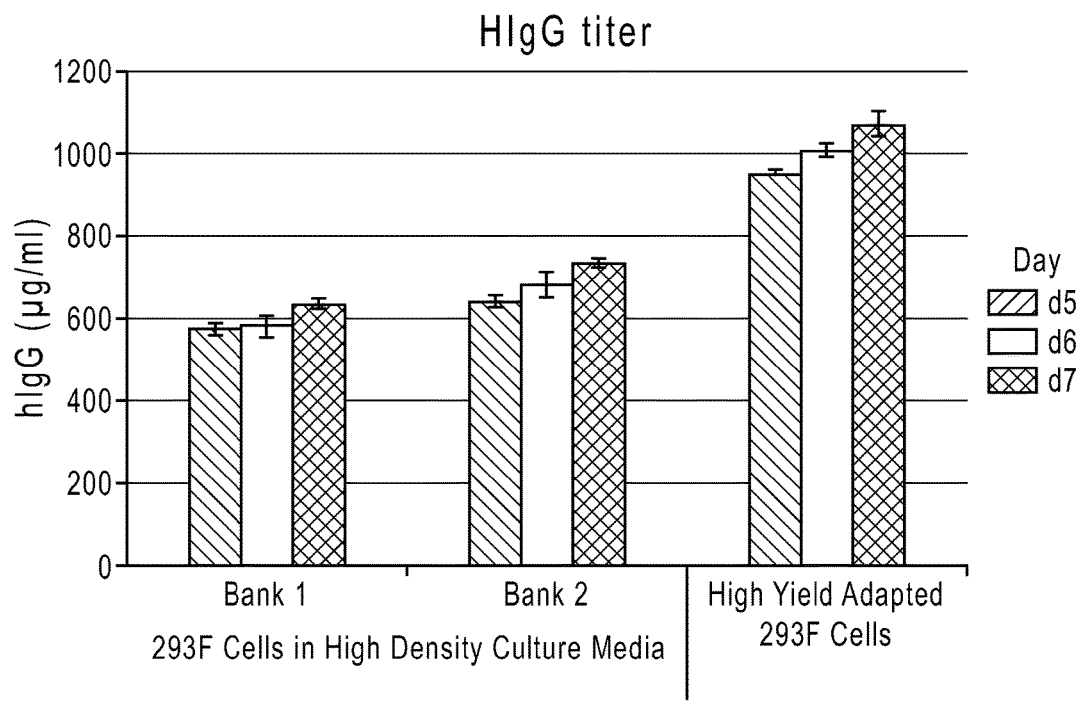
FIG. 2 is a bar graph outlining cell line expression optimization for use with a transient transfection system in accordance with some embodiments of the invention. A parental 293F cell line was slit into multiple subcultures which were subsequently adapted into a High Density Culture Media. Various subcultures that were able to grown at high density were then selected and assessed for their ability to express a recombinant test protein (human IgG). The subculture of cells marked High Yield Adapted 293F Cells (right set of bars) expressed between 35% to 45% more recombinant IgG than two different subcultures of cells derived from the same parental 293F cell line.

FIG. 2 shows a bar graph outlining cell line expression optimization for use with a transient transfection system in accordance with some embodiments of the invention. A parental 293F cell line was slit into multiple subcultures which were subsequently adapted into a High Density Culture Media. Various subcultures that were able to grown at high density were then selected and assessed for their ability to express a recombinant test protein (human IgG). The subculture of cells marked High Yield Adapted 293F Cells (right set of bars) expressed between 35% to 45% more recombinant IgG than two different subcultures of cells derived from the same parental 293F cell line. Thus, it is possible for one skilled in the art to readily obtain a cell line or a derivative of a cell line that has been specifically selected for use with a growth medium, and can be selected based on the ability to facilitate the cultivation of high densities of suspension cells over a defined period of time, without having to replace, supplement or replenish the medium. Such may be accomplished by the skilled artisan without undue experimentation.

Example 3: Transient Transfection is Aided by Expression Enhancers

A panel of chemical additives was tested in combinatorial experiments to evaluate the relative contribution of each component, or the combination of one or more components, to protein yield. A variety of transfection/expression enhancers were identified that significantly improved protein production. Components were formulated into 2 stable Enhancer solutions. Transfection Enhancer 1 (valprioc acid, as defined above) doubles hIgG expression. Enhancer 2 (sodium propionate as defined above) has no strong effect alone, but in combination with Enhancer 1, provides almost 3 fold more hIgG vs. control (with neither Enhancer 1 nor Enhancer 2).

Figure 3:
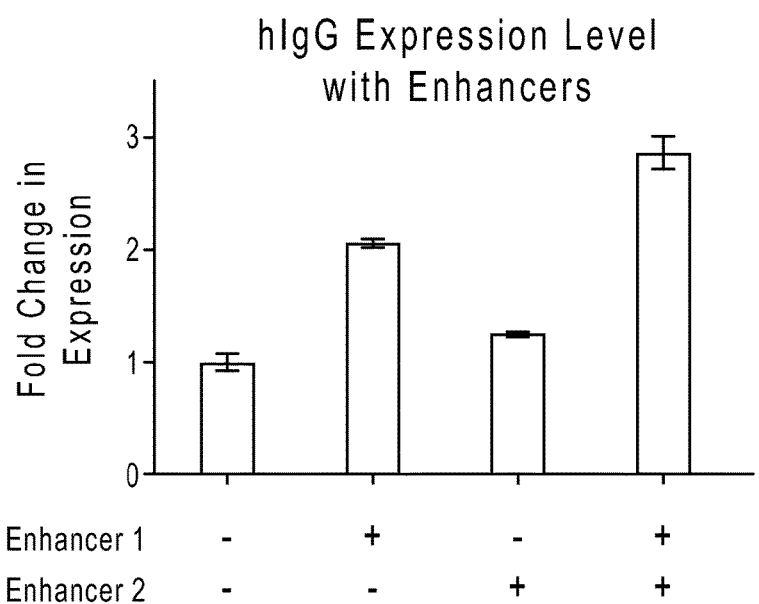
FIG. 3 is a bar graph outlining the effects of various enhancers used in a transient transfection system in accordance with some embodiments. Expression enhancers were identified that significantly improved protein production. Components were formulated into 2 stable Enhancer solutions. The addition of Expression Enhancer 1 doubles hIgG expression (compare first two bars). The addition of Enhancer 2 by itself shows only marginal effect on enhancing expression of IgG, but when added in combination with Enhancer 1, provides almost 3 fold more hIgG vs. control (Compare third and fourth)
Figure 4A:
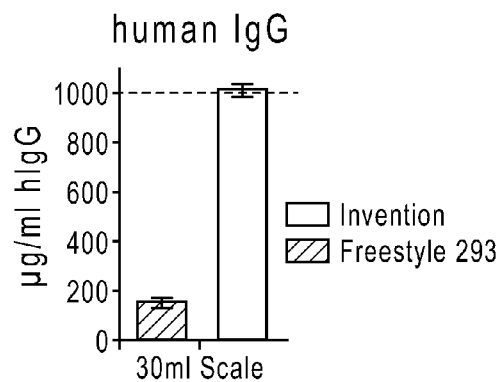
FIG. 4A shows a greater than 5-fold increase in expression of human IgG using the transient transfection system according to some embodiments of the present invention when compared to commercially available Free-Style™ Max system.
Figure 4B:
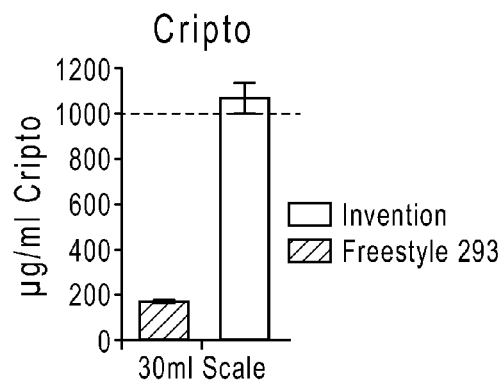
FIG. 4B shows a greater than 5.2-fold increase in expression of Cripto using the transient transfection system according to some embodiments of the present invention when compared to commercially available FreeStyle™ Max system.
Figure 4C:
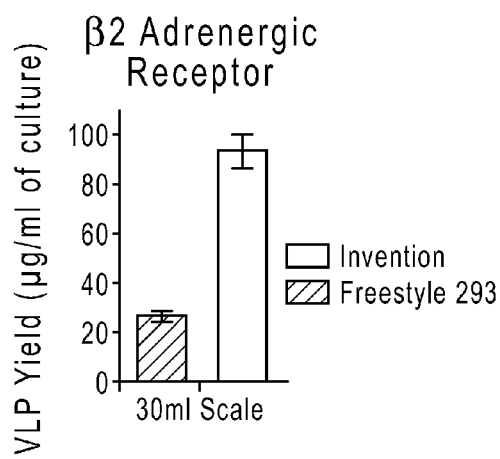
FIG. 4C shows a almost 4-fold increase in expression of 132-adrenergic receptor using the transient transfection system according to some embodiments of the present invention when compared to commercially available FreeStyle™ Max system.
Figure 4D:
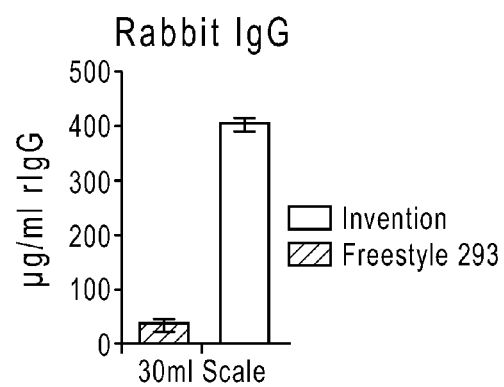
FIG. 4D shows a greater than 11-fold increase in expression of rabbit IgG using the transient transfection system according to some embodiments of the present invention when compared to commercially available FreeStyle™ Max system.
Figure 5:
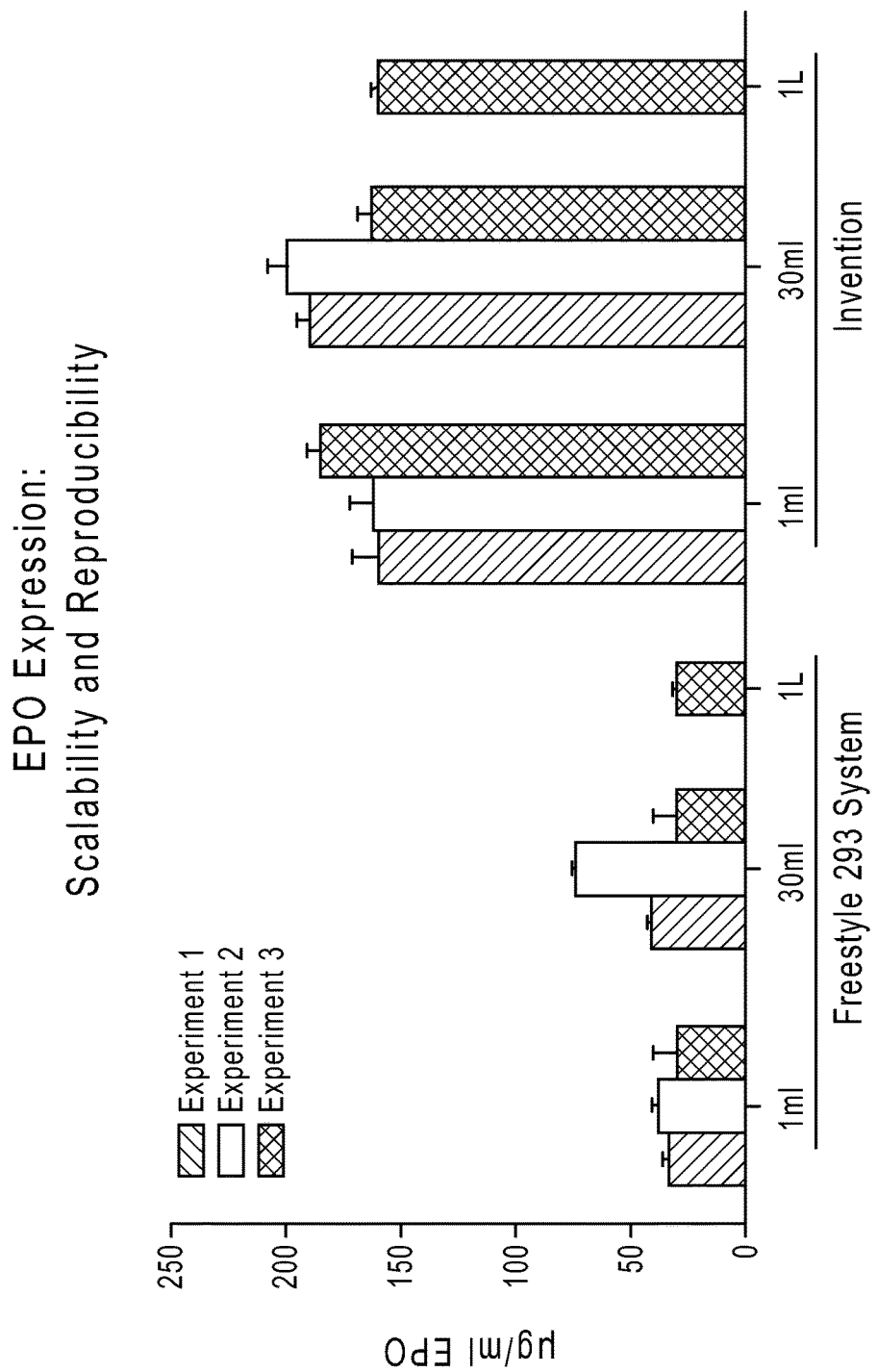
FIG. 5 is a bar graph comparing the expression levels of EPO achieved using a transient transfection system in accordance with some embodiments and a prior art transient transfection system. EPO was expressed using the transient expression system of the present invention and Freestyle™ 293 system. The inventive system is scalable from 1 ml (24-well plate format) up to 1 L (3 L shake flask format). Reliable reproducibility in expression levels of specific proteins was seen in results from three separate analysts in three different labs.

FIG. 3 shows a bar graph outlining the effects of various Enhancer 1 and Enhancer 2 used in a transient transfection system in accordance with some embodiments. Components were formulated into 2 stable Enhancer solutions. The addition of Expression Enhancer 1 doubles hIgG expression (compare first two bars). The addition of Enhancer 2 by itself shows only marginal effect on enhancing expression of IgG, but when added in combination with Enhancer 1, provides almost 3 fold more hIgG vs. control (Compare third and fourth Example 4: Protein Expression Results The transient expression system of the present invention can produce between 1 g/L up to about 2 g/L of human IgG and Cripto. The transient expression system of the present invention system showed between a 3.5×-11.8× increase in transient protein expression of the proteins shown in FIGS. 4A through 4D when compared to the commercially available Freestyle™ 293 system. FIG. 4 shows a comparison of the expression levels of 4 different and unique proteins using a high yield transient transfection system in accordance with some embodiments and a prior art transient transfection system (Freestyle™ 293 system). FIG. 4A shows a greater than 5-fold increase in expression of human IgG using the transient transfection system according to some embodiments of the present invention when compared to commercially available FreeStyle™ Max system. FIG. 4B shows a greater than 5.2-fold increase in expression of Cripto using the transient transfection system according to some embodiments of the present invention when compared to commercially available FreeStyle™ Max system. FIG. 4C shows a almost 4-fold increase in expression of 32-adrenergic receptor using the transient transfection system according to some embodiments of the present invention when compared to commercially available FreeStyle™ Max system. FIG. 4D shows a greater than 11-fold increase in expression of rabbit IgG using the transient transfection system according to some embodiments of the present invention when compared to commercially available FreeStyle™ Max system.

Example 5: EPO Expression, Scalability and Reproducibility

Next, we sought to examine the scalability and reproducibility of the transient transfection system using a widely used expressed protein of clinical importance. Erythropoietin (EPO) was expressed using the transient transfection system of the present invention (bars on right side of graph) and Freestyle™ 293 system (bars on left side of graph). The inventive system is scalable from 1 ml (in 24-well plate format) up to 1 L (3 L shake flask format). Very good reproducibility was seen in results from three separate analysts in three different labs.

CONCLUSIONS 1 g/L expression of two different proteins was achieved using the high yield transient transfection system. High density culture media enabled high density transfection. Significant improvements to transient protein expression were obtained via cell line selection. Transfection enhancers improve transfection and expression at high cell densities. The results are very scalable and reproducible. The transient transfection system of the present invention achieved 3.5×-15-fold increase in protein expression compared to Freestyle™ 293 system.

All publications, patents and patent applications mentioned in this specification are herein incorporated in their entirety by reference into the specification, to the same extent as if each individual publication, patent or patent application was specifically and individually indicated to be incorporated herein by reference. In case of conflict, the specification herein, including definitions, will control. Citation or identification of any reference in this application shall not be construed as an admission that such reference is available as prior art to the present invention.

What is claimed is:

1. A method for producing a recombinant protein in cultured 293 cells, said method comprising:
    obtaining a suspension culture comprising 293 cells in a high density culture medium, said suspension culture having a cell density of between about $2 \times 10^6$ to about $2 \times 10^7$ cells/ml;
    transfecting said 293 cells with an expression vector containing a genetic sequence capable of producing an expressed protein;

incubating said transfected 293 cells for a first period of time;

contacting said transfected 293 cells with at least one expression enhancer composition comprising valproic acid or a salt thereof;

incubating said transfected 293 cells in the presence of said expression enhancer composition for a second period of time such that said vector expresses said protein; and harvesting said transfected 293 cells after said second period of time;

wherein said high density culture medium is not replaced, replenished, or supplemented with fresh media following the transfection step.

2. The method according to claim 1, wherein said cultured 293 cells are a suspension culture adapted for growth under high density conditions.

3. The method according to claim 1, wherein said 293 cells have been adapted for growth under high density conditions.

4. The method according to claim 3, wherein said 293 cells are 293 F cells.

5. The method according to claim 1, wherein the volume of the suspension culture is in the range of about 200 µL to about 5 L.

6. The method according to claim 1, wherein said expression enhancer composition further comprises at least one of sodium propionate, lithium acetate, dimethyl sulfoxide (DMSO), galactose, amino acid mixtures, butyric acid, or any salts or combinations of the aforementioned.

7. The method according to claim 1, wherein the concentration of valproic acid (VPA) is in the range of about 0.20 mM to about 25 mM.

8. The method according to claim 1, wherein the concentration of valproic acid is in the range of about 0.25 mM to about 24 mM.

9. The method according to claim 1, wherein the expression composition further comprises sodium propionate.

10. The method according to claim 9, wherein the final concentration of sodium propionate in the culture is in the range of about 0.2 mM to about 100 mM.

11. The method according to claim 9, wherein the final concentration of sodium propionate in the culture is in the range of about 0.5 to about 80 mM.

12. The method according to claim 1, wherein the expression enhancer composition further comprises lithium acetate (LiAc).

13. The method according to claim 12, wherein the final concentration of LiAc in the culture is in the range of about 0.25 to about 25 mM.

14. The method according to claim 12, wherein the final concentration of LiAc in the culture is in the range of about 0.26 mM to about 20 mM.

15. The method according to claim 1, wherein the expression enhancer composition further comprises butyric acid.

16. The method according to claim 15, wherein the final concentration of butyric acid in the culture is in the range of about 0.25 to about 25 mM.

17. The method according to claim 1, wherein the volume of the suspension culture is in the range of about 25 mL to about 50 L.

18. The method according to claim 1, wherein the volume of the suspension culture is in the range of about 100 mL to about 1 L.

19. The method according to claim 1, wherein the volume of the suspension culture is in the range of about 200 mL to about 500 mL.

20. The method according to claim 1, wherein the cell density of the transfection step is between about $3 \times 10^6$ to about $20 \times 10^6$ cells/ml.

21. The method according to claim 1, wherein the cell density of the transfection step is in the range of about $2 \times 10^6$ to about $6 \times 10^6$.

22. The method according to claim 1, wherein said expression vector comprises a woodchuck hepatitis virus posttranscriptional regulatory (WPRE) element.

23. The method according to claim 1, wherein said high density culture medium is a serum-free/protein-free chemically defined culture medium capable of promoting the growth of transfected cells at cell densities in excess of $2.5 \times 10^6$ cells/ml with cell viability remaining in excess of 80%.

24. The method according to claim 1, further comprising purifying said expressed protein.

25. The method according to claim 1, wherein said cells express one or more expression enhancing proteins.

26. The method according to claim 25, wherein said expression enhancing proteins are selected from the list consisting of AKT, P18, P21, Bcl-$X_L$, and PKBa.

27. The method according to claim 25, wherein said cells transiently express one or more expression enhancing proteins.

28. The method according to claim 25, wherein said cells stably express one or more expression enhancing proteins.

29. The method according to claim 1, wherein said first period of time is in the range of about 2 hrs to about 4 days.

30. The method according to claim 1, wherein said second period of time is in the range of about 10 hrs to about 10 days.

* * * * *